(12) United States Patent
Potyrailo et al.

(10) Patent No.: US 9,274,071 B2
(45) Date of Patent: Mar. 1, 2016

(54) METHODS FOR ASSESSING CELL CULTURE FLUID BY IMPEDANCE SPECTRA

(71) Applicant: General Electric Company, Schenectady, NY (US)

(72) Inventors: Radislav A. Potyrailo, Niskayuna, NY (US); Victoria E. Cotero, Troy, NY (US); Jon A. Dieringer, Des Plaines, NY (US); Thomas J. Erdenberger, Arlington, MA (US); Timothy A. Wortley, Lancaster, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 4 days.

(21) Appl. No.: 14/144,118

(22) Filed: Dec. 30, 2013

(65) Prior Publication Data

US 2015/0185173 A1 Jul. 2, 2015

(51) Int. Cl.
*G01N 27/02* (2006.01)
*C12M 1/34* (2006.01)
*G01N 33/487* (2006.01)

(52) U.S. Cl.
CPC .............. *G01N 27/02* (2013.01); *C12M 41/36* (2013.01); *C12M 41/46* (2013.01); *G01N 27/026* (2013.01); *G01N 33/48735* (2013.01)

(58) Field of Classification Search
None
See application file for complete search history.

(56) References Cited

U.S. PATENT DOCUMENTS

| | | | |
|---|---|---|---|
| 4,652,828 A | 3/1987 | Kenyon et al. | |
| 4,810,650 A | 3/1989 | Kell et al. | |
| 4,876,504 A * | 10/1989 | Blake et al. | 324/204 |
| 4,881,025 A | 11/1989 | Gregory | |
| 4,965,206 A | 10/1990 | Kell | |
| 5,182,193 A | 1/1993 | Mishima et al. | |
| 5,269,175 A | 12/1993 | Chmiel et al. | |
| 5,583,432 A | 12/1996 | Barnes | |
| 6,496,020 B1 | 12/2002 | Davey et al. | |
| 6,664,045 B1 | 12/2003 | Hyldig-Nielsen et al. | |
| 6,861,847 B2 | 3/2005 | Yamagishi et al. | |
| 6,905,838 B1 | 6/2005 | Bittner | |
| 6,965,243 B2 | 11/2005 | Yamagishi et al. | |
| 7,108,980 B1 | 9/2006 | Hyldig-Nielsen et al. | |
| 7,238,496 B2 | 7/2007 | Li et al. | |
| 7,315,767 B2 | 1/2008 | Caduff et al. | |
| 7,507,579 B2 | 3/2009 | Boccazzi et al. | |
| RE41,129 E | 2/2010 | Novak et al. | |
| 7,911,345 B2 * | 3/2011 | Potyrailo et al. | 340/572.1 |
| 8,468,871 B2 * | 6/2013 | Potyrailo et al. | 73/19.01 |
| 2009/0278685 A1 | 11/2009 | Potyrailo et al. | |
| 2012/0045757 A1 | 2/2012 | Kjaerulff et al. | |
| 2012/0231961 A1 | 9/2012 | La Duc et al. | |
| 2013/0023781 A1 | 1/2013 | Freeman et al. | |
| 2014/0182362 A1 * | 7/2014 | Potyrailo et al. | 73/64.53 |
| 2014/0182363 A1 * | 7/2014 | Potyrailo et al. | 73/64.53 |

FOREIGN PATENT DOCUMENTS

| | | |
|---|---|---|
| EP | 0881489 A1 | 12/1998 |
| EP | 1888123 B1 | 1/2013 |
| WO | 8504481 A1 | 10/1985 |
| WO | 0151921 A1 | 7/2001 |

OTHER PUBLICATIONS

Soley et al., "On-line Monitoring of Yeast Cell Growth by Impedance Spectroscopy", Journal of Biotechnology, vol. No. 118, Issue No. 4, pp. 398-405, Sep. 2005.

Zheng et al., "Resonance Impedance Sensing of Human Blood Cells", Sensors and Actuators A, vol. 145-146, pp. 29-36, Jul. 2008.

PCT Search Report and Written Opinion issued in connection with corresponding PCT Application No. PCT/EP2014/078826 on Apr. 8, 2015.

Fernandez-Da-Silva et al., "Viability in protoplasts and cell suspensions of Coffea arabica cv. Catimor", Electronic Journal of Biotechnology, pp. 593-597, vol. 9, Issue 5, 2006.

Clark et al., "Suitability of Selected Single-Use Process Monitoring and Control Technology", Bio Process International, pp. 16-20, vol. 4, Issue 6, Jun. 2006.

Ansorge et al., "On-line monitoring of infected Sf-9 insect cell cultures by scanning permittivity measurements and comparison with off-line biovolume measurements", pp. 115-124, vol. 55, Issue 2-3, Dec. 2007.

Rao et al., "Non-Invasive Sensors as Enablers of "Smart" Disposables", Bio process Sensor Technology, pp. 24-27, vol. 7, Suppl 1, 2009.

Dabros et al., "Cole—Cole, linear and multivariate modeling of capacitance data for on-line monitoring of biomass", Bioprocess and Biosystems Engineering, pp. 161-173, vol. 22, Issue 2, Feb. 2009.

Glindkamp et al., "Sensors in disposable bioreactors status and trends", Adv Biochem Eng Biotechnol, pp. 145-169, vol. 115, 2010.

Opel et al., "Quantitative modeling of viable cell density, cell size, intracellular conductivity, and membrane capacitance in batch and fed-batch CHO processes using dielectric spectroscopy", Biotechnol Prog., pp. 1087-1099, vol. 26, Issue 4, 2010.

Ansorge et al., "Multifrequency permittivity measurements enable on-line monitoring of changes in intracellular conductivity due to nutrient limitations during batch cultivations of CHO cells", Biotechnol Prog., pp. 272-283, vol. 26, Issue 1, 2010.

(Continued)

*Primary Examiner* — Ralph Gitomer
(74) *Attorney, Agent, or Firm* — Fletcher Yoder, P.C.

(57) ABSTRACT

Provided herein are techniques for identification of viable and nonviable cells in a cell culture that include measuring a resonance impedance spectral response of at least one resonator in proximity to the cell culture and correlating the measured response to the concentration of viable cells in cell culture and/or the concentration of nonviable cells in cell culture.

18 Claims, 21 Drawing Sheets

(56) References Cited

OTHER PUBLICATIONS

Justice et al., "Process control in cell culture technology using dielectric spectroscopy", Biotechnol Adv., pp. 391-401, vol. 29, Issue 4, 2011.

Logan et al., "A Biomass Monitor for Disposable Bioreactors", vendor voice, pp. 48-54, vol. 9, Issue 1, Jan. 2011.

Ronnest et al., "Introducing process analytical technology (PAT) in filamentous cultivation process development: comparison of advanced online sensors for biomass measurement", pp. 1679-1690, vol. 38, Issue 10, Oct. 2011.

Logan et al., "Creating new opportunities in process control through radio frequency impedance spectroscopy", vol. 5, suppl 8, Nov. 2011.

* cited by examiner

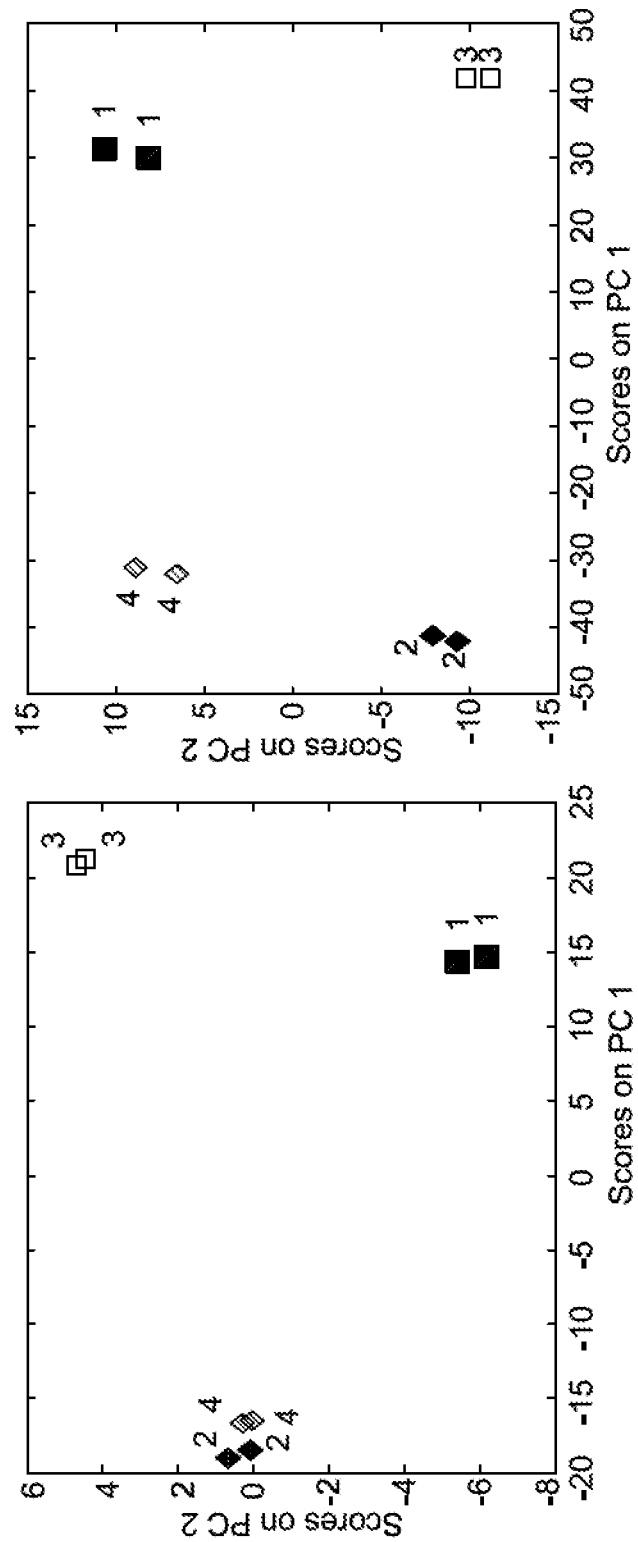

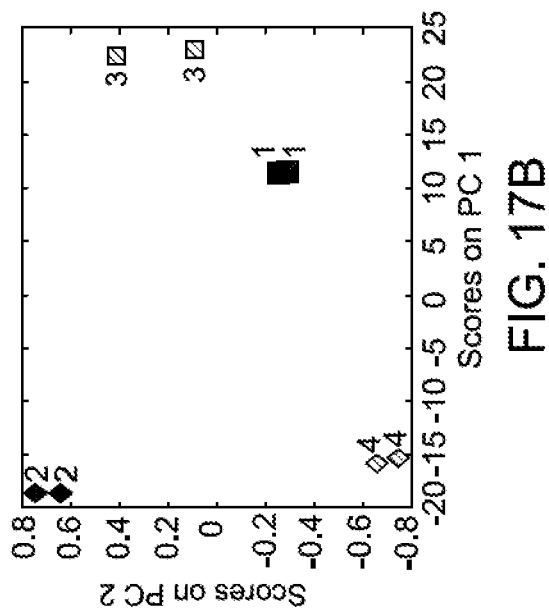
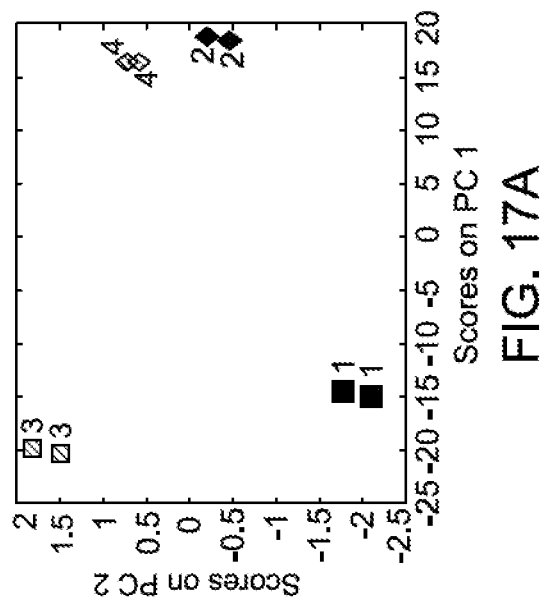
FIG. 17A
FIG. 17B

METHODS FOR ASSESSING CELL CULTURE FLUID BY IMPEDANCE SPECTRA

BACKGROUND

The subject matter disclosed herein relates to cells grown in cell culture and distinguishing between viable and nonviable cells in cell culture in real time.

The self-replicating nature of biological systems may be harnessed to produce materials of interest by growing individual cells or organisms that produce such materials and purifying the desired products from the cell culture. For example, certain drugs or compounds may be produced by cells, either as a natural metabolic product of the cells or via engineered cells, such as cells engineered to produce recombinant proteins. These cells may be grown in large scale reactors to produce high quality biopharmaceuticals. In such reactors, the manufacturing parameters are monitored using in-line sensors and off-line (i.e., not in-line but in the laboratory, not connected to the reactors) analytical systems. Monitoring of critical manufacturing parameters may be performed upstream (before the bioreactor), in the bioreactor, and downstream (after the bioreactor). Parameters that are typically continuously monitored include parameters that influence growth conditions, such as temperature, solution conductivity, pressure, pH, glucose concentration, dissolved oxygen, and viable cell mass, and are monitored in a similar manner in both single-use and in conventional stainless steel manufacturing systems. Other parameters, such as cell viability, lactate, glutamine, osmolality, pyruvate, amino acids, product purity, and trace elements are typically not measured in-line, because of difficulties of measurements using existing sensors. Instead, these parameters are typically measured "off line" by extracting samples from the reactors and further analyzing these samples outside of the reactor using laboratory analytical instruments.

BRIEF DESCRIPTION

In one embodiment, a method for analyzing a cell culture reaction is provided. The method includes generating a plurality of frequencies with a sensor comprising a sensing region in operational contact with the cell culture reaction fluid and a plurality of tuning circuits outside the fluid; receiving a signal from the sensor, wherein the signal is representative of impedance spectra of the sensing region in operational contact with the cell culture reaction fluid over a measured spectral frequency range; analyzing the impedance spectra; and determining one or more properties of the cell culture reaction fluid based on the analyzed impedance spectra. The method includes generating multiple frequencies with a sensor comprising at least one resonant circuit, wherein the sensor is in operational contact with a cell culture reaction fluid; receiving a signal from the sensor, wherein the signal is representative of an impedance spectrum of the cell culture reaction over a measured spectral frequency range; analyzing at least three spectral parameters of the impedance spectrum; and correlating at least three spectral parameters to a concentration of viable and nonviable cells in the cell culture reaction based on the spectral parameters.

In another embodiment, a method for analyzing a cell culture reaction with enhanced selectivity is provided. The method includes generating multiple frequencies with a sensor comprising a sensing region that is in operational contact with a cell culture reaction fluid and a plurality of tuning circuits outside the cell culture reaction fluid that provide resonances over the frequency range of spectral beta-dispersion of the cell culture, wherein the sensor is in contact with a cell culture reaction; receiving a signal from the sensor, wherein the signal is representative of resonance impedance spectra of the cell culture reaction over a measured spectral frequency range; analyzing at least six spectral parameters of the resonance impedance spectrum; and correlating the linear combination of the spectral parameters to a concentration of viable and nonviable cells in the cell culture reaction based on the spectral parameters.

In another embodiment, a method for analyzing a cell culture reaction is provided. The method includes generating multiple frequencies with a sensor comprising a sensing region that is protected from a direct contact with the analyzed fluid by the use of a dielectric conformal layer or a dielectric protective layer (e.g., 10 nanometers to 10 millimeters in thickness, in a non-limiting example) and a plurality of tuning circuits outside the cell culture reaction fluid that provide resonances over the frequency range of spectral dispersions of the cell culture, wherein the sensor with the dielectric conformal protective layer is in contact with a cell culture reaction; receiving a signal from the sensor, wherein the signal is representative of resonance impedance spectra of the cell culture reaction over a measured spectral frequency range; analyzing at least six spectral parameters of the resonance impedance spectrum; and correlating the linear combination of the spectral parameters to a concentration of viable and nonviable cells in the cell culture reaction based on the spectral parameters. A sensor comprising a sensing region and at least one tuning circuit forms a resonant circuit structure or a resonator. The dielectric conformal layer is biologically compatible with the fluid and cell culture of the cell culture reaction. Other parameters, such as cell viability, lactate, glutamine, osmolality, pyruvate, amino acids, product purity, and trace elements may also be assessed. For example, in an antibody production reaction, increased osmolality in the context of decreased cell growth occurs during increased antibody production.

In another embodiment, a method for analyzing a cell culture reaction in a single-use container with a single-use sensor is provided. The method includes calibration of at least one sensor from the fabricated batch of sensors using known calibration standards, establishing calibration transfer relations between sensors in the fabricated batch based on the manufacturing tolerances of the sensors manufacturing, recording calibration coefficients into the memory of each sensor in the fabricated batch, integrating the sensors into single-use containers, applying a sterilization step for the containers with the integrated sensors, operating container for cell culture, and monitoring the concentration of viable and nonviable cells in the cell culture reaction using the integrated sensors. In other embodiments, sensors may be multi-use and, further, may be tuned to one or more growth media depending on their desired use.

In another embodiment, a method for analyzing a cell culture reaction is provided. The method includes providing a sensor comprising at least one resonant circuit; exposing the sensor to the cell culture reaction; probing the cell culture reaction with at least one resonance generated by the sensor; determining at least one resonance impedance spectrum of the sensor response over a measured spectral frequency range of the sensor; applying multivariate statistical analysis to the at least one resonance impedance spectrum of the sensor response to obtain multivariate response factors; and relating the multivariate response factors to concentrations of viable cells and nonviable cells in the cell culture reaction.

In another embodiment, a method for analyzing a cell culture reaction is provided. The method includes providing a sensor comprising at least one resonant circuit; exposing the sensor to the cell culture reaction; probing the cell culture reaction with at least one resonance generated by the sensor; determining at least one resonance impedance spectrum of the sensor response over a measured spectral frequency range of the sensor; applying multivariate statistical analysis to the at least one resonance impedance spectrum of the sensor response to obtain multivariate response factors; and relating the multivariate response factors to concentration of viable cells, size of the viable cells, and concentration of nonviable cells in the cell culture reaction.

In another embodiment, a system is provided that includes a sensor comprising at least one resonant circuit and at least two electrodes, wherein the sensor is configured to generate a signal representative of an impedance spectrum over a measured spectral frequency range. At least two electrodes form a sensing electrode structure. The sensing electrode structure can be bare and in direct contact with the cell culture reaction fluid or the sensing electrode structure can be conformally coated with a dielectric protective coating. A sensor comprising a sensing region and at least one tuning circuit forms a resonant circuit structure. The system also includes a memory that stores calibration coefficients of the sensor for quantitation of viable and nonviable cells and a memory that stores instructions for: receiving the signal from the sensor; analyzing two or more spectral parameters of the impedance spectrum based on the signal; and correlating the two or more spectral parameters to a concentration of viable and nonviable cells in the cell culture reaction based on the spectral parameters; and a processor configured to execute the instructions.

In another embodiment, a system is provided that includes a sensor comprising at least one sensing region and a plurality of tuning circuits that provide at least three resonances over the frequency range of spectral dispersions of the cell culture, wherein the sensor is in contact with a cell culture reaction. The system also includes a memory storing instructions for: generating multiple frequencies with the sensor; receiving a signal from the sensor, wherein the signal is representative of resonance impedance spectra of the cell culture reaction over a measured spectral frequency range; analyzing at least six spectral parameters of the resonance impedance spectrum; and correlating the linear combination of the spectral parameters to a concentration of viable and nonviable cells in the cell culture reaction based on the spectral parameters; and a processor configured to execute the instructions.

In another embodiment, a system is provided that includes a sensor comprising at least one sensing region that is protected from a direct contact with the analyzed fluid by the use of a dielectric conformal layer that is biologically compatible with the cells in the reaction and a plurality of tuning circuits that provide at least three resonances over the frequency range of spectral dispersions of the cell culture, a sensor reader to read the response of the sensor across predetermined frequency ranges of the resonances, and a processor for analyzing at least six spectral parameters of the resonance impedance spectra and correlating the linear combination of the spectral parameters to a concentration of viable and nonviable cells in the cell culture reaction based on the spectral parameters.

In another embodiment, a system for analyzing a cell culture reaction is provided that includes a single-use sensor comprising at least one resonant circuit and at least two electrodes, wherein the sensor is configured to generate a signal representative of an impedance spectrum over a measured spectral frequency range. The system also includes a memory that stores calibration coefficients of the sensor for quantitation of viable and nonviable cells and a memory that stores instructions for: receiving the signal from the sensor; analyzing two or more spectral parameters of the impedance spectrum based on the signal; and correlating the two or more spectral parameters to a concentration of viable and nonviable cells in the cell culture reaction based on the spectral parameters; and a processor configured to execute the instructions.

In another embodiment, a system for analyzing a cell culture reaction in a single-use container (e.g., flask, microtiter well plate, etc.) with a single-use sensor is provided that includes a resonant sensor assembly on a dielectric substrate having a sensing region. The sensor assembly further comprises a plurality of tuning elements operatively coupled to the sensing region, wherein the sensing region is coupled to the plurality of tuning elements to define a plurality of resonant circuits.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 13A depicts the PCA scores plot of PC1 vs. PC2 upon exposure of sensor to four solutions and performing conventional impedance measurements;

FIG. 13B depicts the PCA scores plot of PC1 vs. PC2 upon exposure of sensor to four solutions and performing resonance impedance measurements;

FIG. 17A depicts the PCA scores plot of PC1 vs. PC2 upon measurements of four solutions using a sensor with an inter-digital electrode structure with the electrode width and the spacing between electrodes of 0.3 mm and no dielectric protective coating as measured with conventional impedance;

FIG. 17B depicts the PCA scores plot of PC1 vs. PC2 upon measurements of four solutions using a sensor with an inter-digital electrode structure with the electrode width and the spacing between electrodes of 0.3 mm and with a 0.25 micrometers thick dielectric protective coating as measured with conventional impedance;

DETAILED DESCRIPTION

Figure 1:
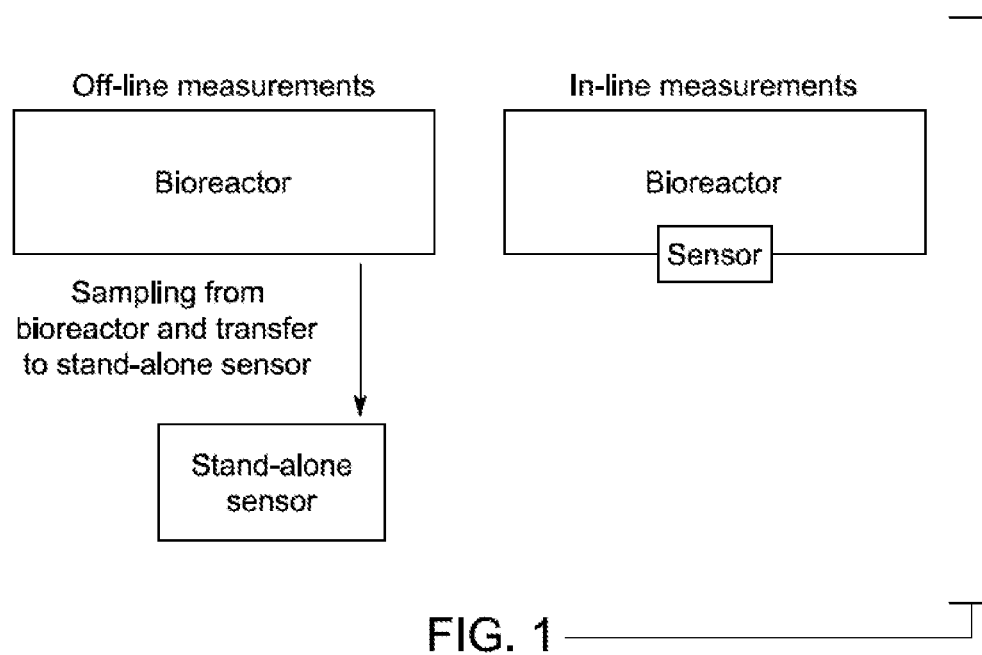
FIG. 1 is a general schematic for performing off-line and in-line measurements according to an embodiment of the disclosure.

The present sensing techniques facilitate simultaneous independent and real time determination of viable and nonviable cells using a sensor directly in a cell culture. Real time identification and quantitation of both viable and nonviable cells in bioreactors using in-line sensors without the need for periodic sampling of the bioreactor is beneficial for biopharmaceutical process operations. At present, assessing a parameter such as cell mass is performed with cell mass sensors that provide information only about the viable cells and do not provide additional information about the populations and concentrations of viable as well as nonviable cells in cell culture. Further, integrating increased functionality with in-line sensors provides the benefit of increased sterility and decreased opening of reaction containers for sampling. As depicted in FIG. 1, when sampling from a reaction container (bioreactor) is performed, the sample is further transferred to a stand-alone sensor for off-line analysis. The off-line analysis has the risk of contamination of the reaction container because of the periodic sampling. The off-line analysis also requires the removal of a certain fluid volume from the reaction container for the off-line analysis. Unlike these problems with off-line analysis, the in-line analysis does not have these limitations, eliminates the risk of culture contamination due to the periodic sampling, and facilitates an increased sterility.

Conventional measurements of concentration of viable cells (also known as cells biomass) rely on capacitance measurements at given frequencies or rely on the scanning dielectric spectroscopy or scanning radio-frequency spectroscopy. The viable cells have intact plasma membranes and contribute to the change in the relative permittivity of the cell culture of the beta-dispersion frequency range of cells. In contrast, the nonviable cells have leaky membranes that do not contribute to the change in the relative permittivity of the cell culture of the beta-dispersion frequency range of cells and, thus, do not produce change in the capacitance signal.

One technique for assessing viable cell concentration is the changes in capacitance or the relative permittivity. The relative permittivity is calculated from the capacitance measurements taking into the account the physical constant of the electrodes of the sensor. Another technique is the inductive dielectric spectroscopy where the electrodes are assembled as toroidal coils and are separated from each other by the liquid. The geometrical parameters of toroidal coils are inner and outer coil diameters, coil thickness, and coil-to-coil separation distance. Yet another technique of measurements of dielectric properties of samples involves resonator methods. However, such techniques cannot quantify concentrations of viable and nonviable cells. The bulk conductivity of the cell culture depends on many fermentation factors even at the constant concentration of viable cells when the concentration of viable cells reaches the saturation.

Provided herein are techniques for identification and quantitation of viable and nonviable cells in a culture that include measuring a resonance impedance spectral response of at least one resonator in proximity to the cell culture and correlating the first measured resonance impedance sensor response to the concentration of viable cells in cell culture; and correlating a second measured sensor resonance impedance response to the concentration of nonviable cells in cell culture.

Figure 2:
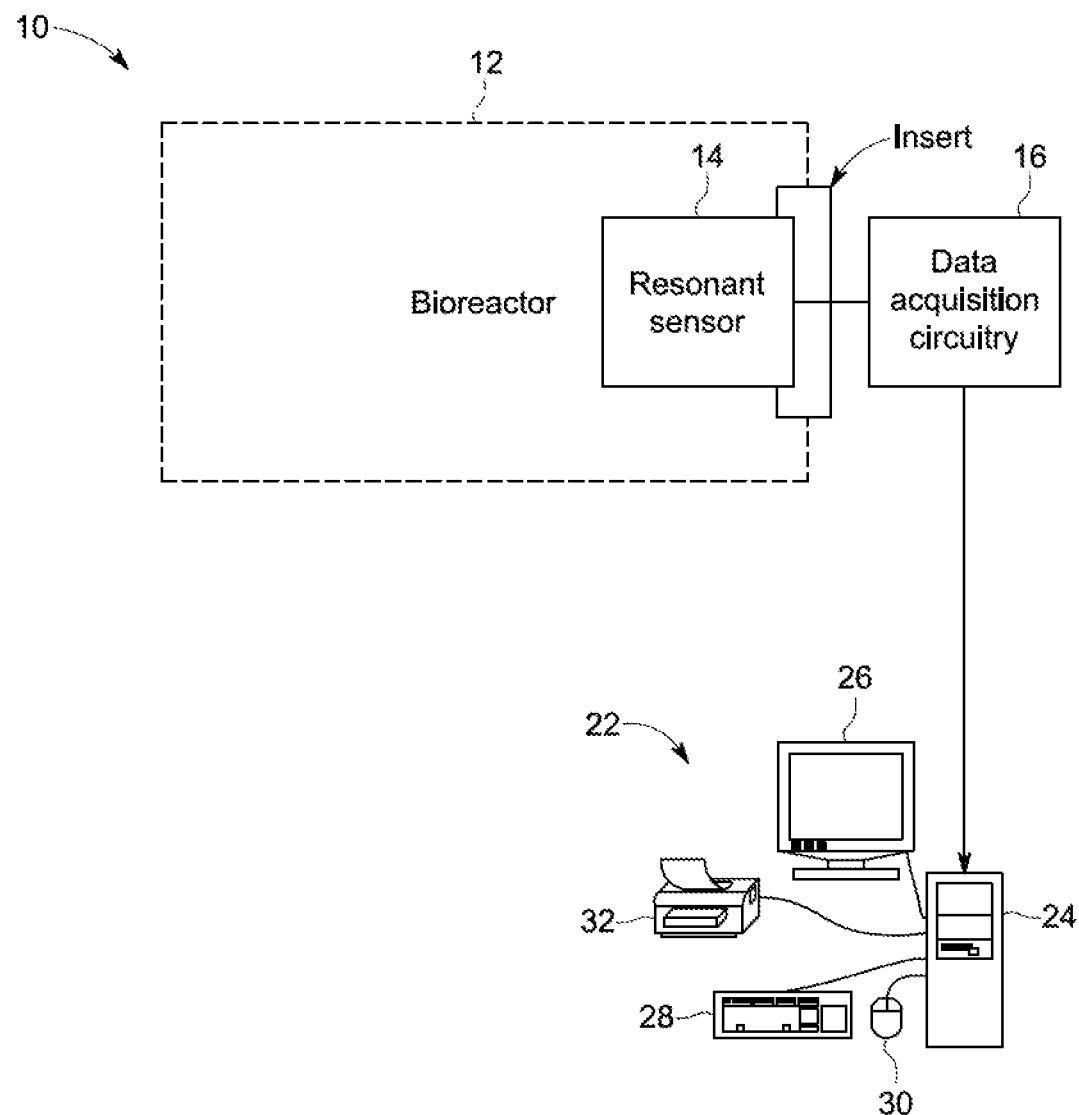
FIG. 2 is a block diagram of a system for determining viable and nonviable cells in cell culture according to an embodiment of the disclosure.

The disclosed embodiments may be used for simultaneous in-situ independent determination of viable and nonviable cells in cell culture of any scale. A cell culture reaction may mean a fluid undergoing a process to form a cell culture, such that sensors as disclosed may be in contact with a fluid undergoing a reaction process. The cell culture may be in an industrial or lab scale reactor or, alternatively, may take place in small scale reactors or microtiter well plates. The cell culture fluid may include the medium (e.g., a liquid or gel containing suitable nutrient sources such as amino acids, glucose, salts, etc.) and cells. The cell culture fluid can be related to the fermentation of different cells. Nonlimiting examples of fermentation of cells include animal cells, mammalian cells, plant cells, bacteria, yeasts, fungi. The fermentation is performed in a batch or in a continuous mode. According to the present techniques, information about concentrations of viable and nonviable cells is obtained without disturbing the fermentation process and without taking samples for off-line analysis of cells. For example, the embodiments may be used in conjunction with systems that include a bioreactor, at least one resonant sensor, a sensor reader, and a data processor. To that end, FIG. 2 illustrates a system 10 for assessing cells that includes a bioreactor 12 and an in-line resonant sensor 14. The resonant sensor 14 may be disposed in or on the bioreactor 12 or may be coupled to in-line medical tubing or connectors in fluid communication with the bioreactor 12. In particular embodiment, the resonant sensor 14 is configured to provide continuous or intermittent monitoring of the cell growth within the bioreactor. The bioreactor 12 may be any suitable cell culture reaction vessel that facilitates cell growth. For example, the bioreactor may be a large or small-scale reactor, a bag reactor, a tank reactor, etc.

Figure 3:
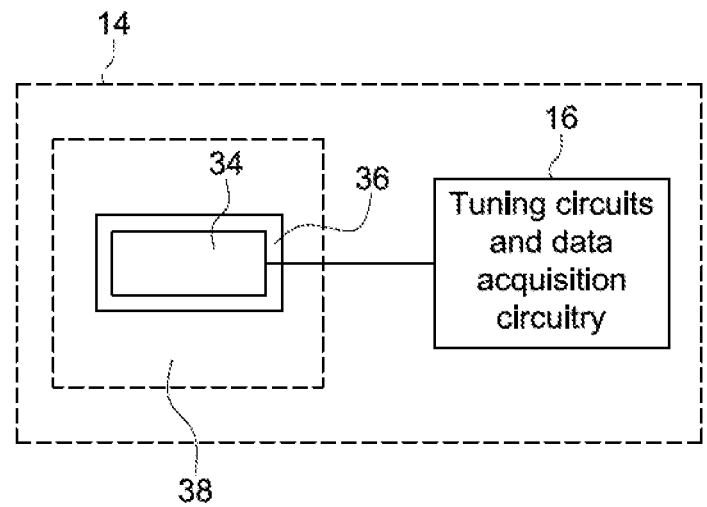
FIG. 3 is a schematic view of a resonant sensor according to an embodiment of the disclosure.

The resonant sensor 14 is configured to detect chemical, physical or biological parameters of a sample via the resonance impedance spectral response of at least one resonator or resonant circuit. As opposed to simple impedance measurements, the disclosed embodiments use the sample to be probed with at least one resonant electrical circuit. The resonance impedance spectrum of the sensor in proximity to the sample (the sensor in the operational contact with a cell culture reaction fluid) varies based on sample composition. The measured resonance impedance values Z' (which is the real part of impedance, Zre) and Z" (which is the imaginary part of impedance, Zim) reflect the response of the cell culture sample (for example, the portion of the cell culture in proximity to the sensor 14) to a stimulus of the electric field of the resonant electrical circuit. The electrical field may be applied by the sensor 14 via electrodes, which may be in direct or indirect electrical contact with the sample. For example, a resonant sensor may be a combination of a sensing region and tuning circuits. The sensing region is either bare or coated with a protective dielectric layer (e.g., as shown in the embodiment of FIG. 3). In both cases, the sensing region may be considered to be in "operational contact" with cell culture fluid. In such embodiments, the tuning circuits are not in operational contact with cell culture fluid. Indirect electrical contact with the sample is when sensing electrode structure is conformally coated with a dielectric protective coating and when the electric field that is generated between the electrodes interacts with the cell culture reaction fluid after penetrating through the dielectric protective coating.

The resonant sensor 14 may be configured as disclosed in U.S. patent application Ser. Nos. 13/729,800 and 13/729,851 to Potyrailo et al., and filed on Dec. 28, 2012, which are incorporated by reference herein in their entirety for all purposes. In one embodiment, the resonant sensor 14 may be a single use sensor that is used during all or part of a reaction process. For example, during a single reaction, the resonant sensor 14 may come into operational contact with the cell culture and, therefore, be unsuitable for use in other reactions. Further, the resonant sensor 14 may be associated with a particular reactor and may be cleaned and sterilized or replaced according to a maintenance schedule. For example, the resonant sensor 14 may include one or more pairs of electrodes and one or more tuning elements, e.g., a resistor, a capacitor, an inductor, a resonator, impedance transformer, or combinations thereof to form an inductor-capacitor-resistor (LCR) resonant circuit operated at at least one resonant frequency. In certain embodiments, different resonant circuits of a plurality of resonant circuits of a resonant sensor 14 may be configured to resonate at different frequencies.

The different resonant circuits may be configured to probe the growing cells in the bioreactor 12 with a plurality of frequencies. Further, the different frequencies may be used to probe a fluid sample at different depths allowing for use in either adhered or suspension cell culture systems. In certain embodiments, an integrated circuit memory chip may be galvanically coupled to the resonant sensor 14. The integrated circuit memory chip may contain different types of information. Nonlimiting examples of such information in the memory of the integrated circuit chip include calibration coefficients for the sensor, sensor lot number, production date, end-user information. In another embodiment, the resonant sensor 14 is an interdigital structure that is a part of the resonator and has a sensing region for detection of cells in the culture. Turning back to FIG. 2, data from the resonant sensor 14 may be acquired via data acquisition circuitry 16, which may be associated with the sensor 14 or which may be associated with a control system, such as a monitor or workstation 22 including data processing circuitry, where additional processing and analysis may be performed. The data acquisition circuitry 16 can be within the bioreactor 12 as shown in FIG. 2 or can be within the workstation 22. Further, the workstation 22 can be replaced with the control system of the whole bioprocess factory (not shown in FIG. 2) where the resonant sensor 14 and its data acquisition circuitry 16 are connected to the control system of the whole bioprocess factory. The data acquisition circuitry 16 may be in the form of a sensor reader, which may be configured to communicate wirelessly with the bioreactor 12 and/or the workstation 22. For example, the sensor reader may be a battery-operated device.

In addition, the data acquisition circuitry 16 may receive data for one or more resonant sensors 14, (e.g. multiple sensors formed in an array or multiple sensors positioned at different locations in or around the bioreactor 12). The data may be stored in short or long term storage devices, such as archiving communication systems, which may be located within or remote from the system 10 and/or reconstructed and displayed for an operator, such as at the operator workstation 22. Nonlimiting examples of positioning and installations of sensors and sensor systems of the present techniques include bioreactors, individual wells of microtiter well plates, connectors, flow-through components, and any other relevant bioprocess components.

In addition to displaying the data, the operator workstation 22 may control the above-described operations and functions of the system 10. The operator workstation 22 may include one or more processor-based components, such as general purpose or application specific computers 24. In addition to the processor-based components, the computer 24 may include various memory and/or storage components including magnetic and optical mass storage devices, internal memory, such as RAM chips. The memory and/or storage components may be used for storing programs and routines for performing the techniques described herein that are executed by the operator workstation 22 or by associated components of the system 10. Alternatively, the programs and routines may be stored on a computer accessible storage and/or memory remote from the operator workstation 22 but accessible by network and/or communication interfaces present on the computer 24. The computer 24 may also comprise various input/output (I/O) interfaces, as well as various network or communication interfaces. The various I/O interfaces may allow communication with user interface devices, such as a display 26, keyboard 28, mouse 30, and printer 32, that may be used for viewing and inputting configuration information and/or for operating the imaging system 10. The various network and communication interfaces may allow connection to both local and wide area intranets and storage networks as well as the Internet. The various I/O and communication interfaces may utilize wires, lines, or suitable wireless interfaces, as appropriate or desired.

FIG. 3 illustrates a non-limiting example of a design of the resonant sensor 14. A sensing electrode structure 34 of the sensor is connected to the tuning circuits (see FIG. 4) and the data acquisition circuitry 16. The sensing electrode structure 34 can be bare and in direct contact with the cell culture reaction fluid. The sensing electrode structure can be conformally coated with a dielectric protective coating 36. The sensing electrode structure 34 without or with the conformal dielectric protective coating 36 forms a sensing region 38. The sensing electrode structure 34 without or with the conformal dielectric protective coating 36 that forms a sensing region 38 is in operational contact with a cell culture reaction fluid. An "operational contact" of a sensing electrode with a cell culture reaction fluid may refer to embodiments in which the sensing electrode structure 34 is either without (bare) or with the conformal dielectric protective coating 36.

When the sensing electrode structure 34 is bare, the electric field that is generated between the electrodes interacts directly with the cell culture reaction fluid. When the sensing electrode structure is conformally coated with a dielectric protective coating 36, the electric field that is generated between the electrodes interacts with the cell culture reaction fluid after penetrating through the dielectric protective coating 36.

Figure 4:
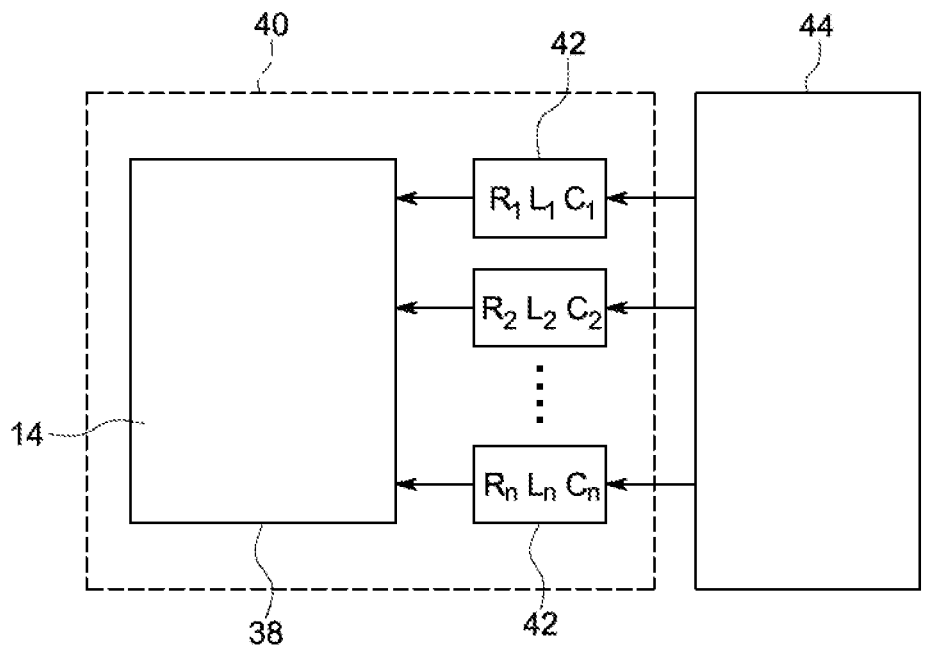
FIG. 4 is a schematic view of a portion of an example sensor system employing a sensor assembly configured for in-line sensing of a cell culture reaction fluid using a plurality of frequencies, in accordance with embodiments of the present disclosure.

FIG. 4 illustrates a portion of a resonant sensor system employing a sensor assembly 40 configured to probe a fluid sample such as cell culture reaction fluid using a plurality of frequencies. The resonant sensor assembly 40 includes the resonant sensor 14. The sensor comprises a single sensing region 38. The sensing region 38 may be disposed on a substrate. In some embodiments, the substrate of the sensor 14 may be a dielectric substrate. The substrate may be a microtiter well plate. In this embodiment, the electrodes may be deposited on the microtiter well plate. A well of a microtiter well plate is a non-limiting example of an open sample container or an open flow-channel.

In certain embodiments, the sensor assembly 40 further includes a plurality of tuning elements 42. The plurality of tuning elements may be operatively coupled to the single sensing region 38 to define a plurality of resonant circuits. The tuning elements 42 along with the single sensing region 38 may define a plurality of resonant circuits. Each resonant circuit of the plurality of resonant circuits may include one or more tuning elements of the plurality of tuning elements.

In the illustrated embodiment, the plurality of tuning elements 42 is external to the sensor 14. However, in one embodiment, the tuning elements 42 may be disposed on the substrate of the sensor 14. In another embodiment, some of the plurality of tuning elements 42 may be external to the sensor substrate, while other tuning elements 42 may be disposed on the substrate. The tuning elements 42 may comprise a resistor, a capacitor, an inductor, a resonator, impedance transformer, or combinations thereof.

Each resonant circuit may be configured to resonate at a particular frequency. At least one resonant circuit may be configured to resonate at a frequency that is different from the resonating frequency of the other resonant circuits. By way of example, if the sensing region 38 includes a pair of electrodes, the tuning elements 42 may be a resistor, a capacitor, and an inductor to form an inductor-capacitor-resistor (LCR) resonant circuit. The tuning elements 42 may be electrically coupled to the sensing region 38. In one embodiment, the tuning elements 42 may be in parallel connection to the sensing region 38. In certain embodiments, the different resonant circuits of the plurality of resonant circuits may be configured to resonate at different frequencies. The different resonant circuits may be configured to probe the fluid sample with a plurality of resonant frequencies. The different resonant frequencies may be used to probe a fluid sample over the frequency range of spectral dispersions of the cell culture. The spectral dispersions of the cell culture that are monitored with the sensors of the present disclosure are over the frequency range from 0.1 Hz to 100 GHz and include alpha, beta, gamma, and delta spectral dispersions.

In the illustrated embodiment, the sensor assembly 10 may also include a multiplexer 44. The multiplexer 44 may be configured to facilitate electronic switching between the plurality of tuning elements 42. The multiplexer 44 may be configured to select one or more signals associated with the probing frequencies and forward the selected signal to an output device or a reader. In one embodiment, the multiplexer 44 may be configured to selectively send signals to an output device or a reader. The multiplexer 44 may be configured to send a plurality of signals simultaneously to a sensor reader.

Figure 5A:
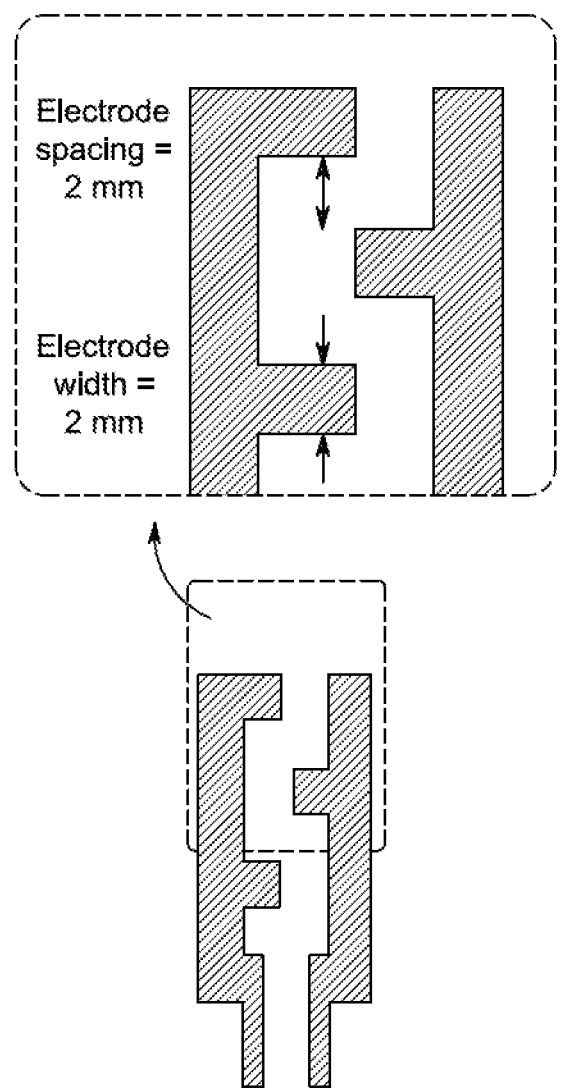
FIG. 5A is a sensing region of a sensor for detection of viable and nonviable cells where the sensing region is an interdigital electrode structure with the electrode width and the spacing between electrodes of 2 mm and sensing area of 2×1 cm.
Figure 5B:
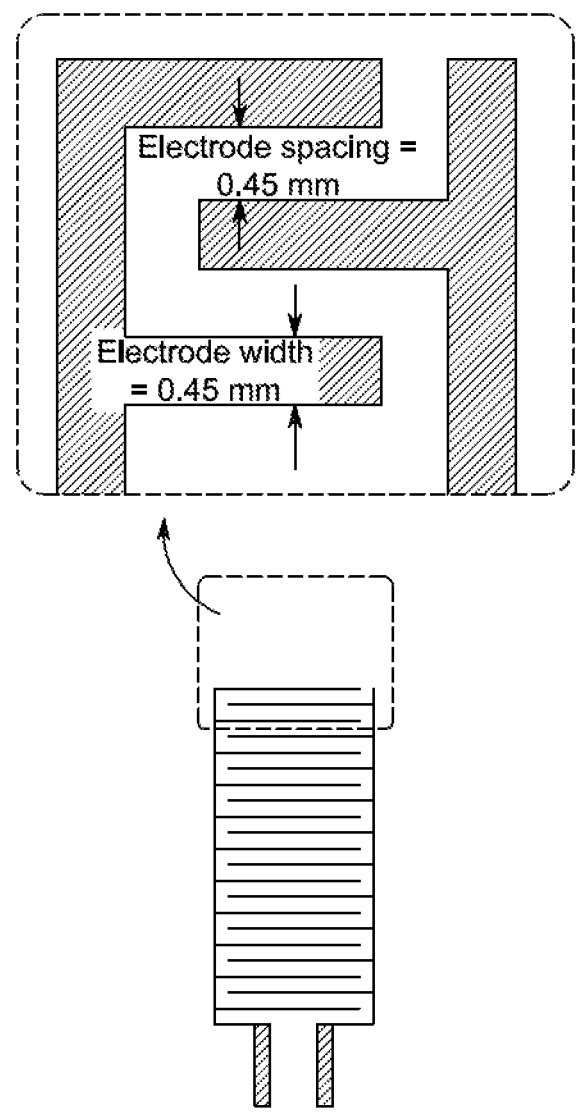
FIG. 5B is a sensing region of a sensor for detection of viable and nonviable cells where the sensing region is an interdigital electrode structure with the electrode width and the spacing between electrodes of 0.45 mm and sensing area of 2×1 cm.
Figure 5C:
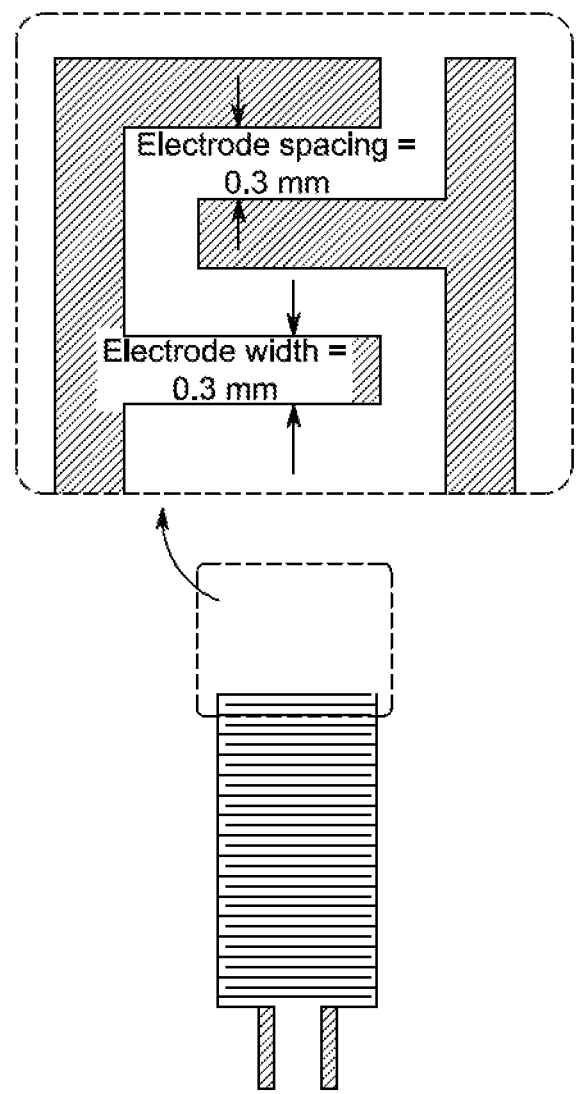
FIG. 5C is a sensing region of a sensor for detection of viable and nonviable cells where the sensing region is an interdigital electrode structure with the electrode width and the spacing between electrodes of 0.30 mm and sensing area of 2×1 cm.

FIGS. 5A, B, and C illustrate non-limiting examples of electrode designs. These electrodes are interdigital (interdigitated) electrode structures with the equal electrode width and the spacing (gap) between electrodes where the spacing between electrodes can be same or different in different directions as well known in the art. FIG. 5A depicts a sensing region of a sensor for detection of viable and nonviable cells where the sensing region is an interdigital two-electrode structure with the electrode width and the spacing between electrodes of 2 mm and sensing area of 2×1 cm. FIG. 5B depicts a sensing region of a sensor for detection of viable and nonviable cells where the sensing region is an interdigital two-electrode structure with the electrode width and the spacing between electrodes of 0.45 mm and sensing area of 2×1 cm. FIG. 5C depicts a sensing region of a sensor for detection of viable and nonviable cells where the sensing region is an interdigital two-electrode structure with the electrode width and the spacing between electrodes of 0.3 mm and sensing area of 2×1 cm.

Other known examples of interdigital electrodes that can be used include electrode structures with variable electrode width and the spacing between electrodes, tapered electrodes, circular electrodes, and others known in the art. The sensor as provided may have at least two electrodes, but also can have four electrodes or more electrodes.

The resonant sensor 14 is positioned in the operational contact with the cell culture reaction fluid. At least one sensor generating a plurality of frequencies is inserted or mounted onto a non-rigid, flexible container via at least one hose barb port or any other mounting device such that the sensor is held aseptically within the internal space of the container and is in operational contact with fluid within the container. The sensor 14 is further connected to a reader device external to the non-rigid, flexible container by direct electrical connection or remote means. In one embodiment, the non-rigid, flexible container is a bioreactor. In another embodiment, a bioreactor is a rigid, non-flexible container.

FIG. 6A-D depict examples of bioreactor-integrated sensors for detection of viable and nonviable cells. In one embodiment depicted in FIG. 6A, the resonant sensor 14 is assembled into an insert. The assembly of the resonant sensor with the insert is further integrated into the bioreactor using a hose barb port. The sensing region of this sensor desirably extends into the bioreactor for at least 10 millimeters.

Figure 6:
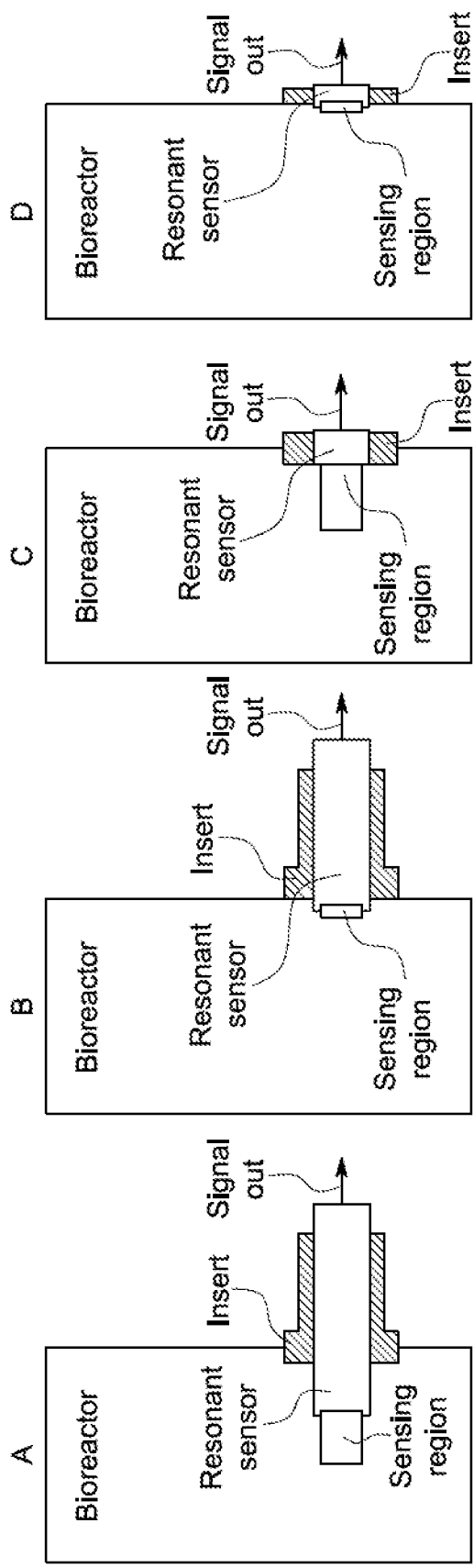
FIG. 6A is an example of a bioreactor-integrated sensor for detection of viable and nonviable cells according to an embodiment of the disclosure.
FIG. 6B is an example of a bioreactor-integrated sensor for detection of viable and nonviable cells according to an embodiment of the disclosure.
FIG. 6C is an example of a bioreactor-integrated sensor for detection of viable and nonviable cells according to an embodiment of the disclosure.
FIG. 6D is an example of a bioreactor-integrated sensor for detection of viable and nonviable cells according to an embodiment of the disclosure.

In another embodiment depicted in FIG. 6B, the resonant sensor is assembled into an insert. The assembly of the resonant sensor with the insert is further integrated into the bioreactor using a hose barb port. The sensing region of this sensor desirably extends into the bioreactor for at most 2 millimeters.

In another embodiment depicted in FIG. 6C, the resonant sensor is assembled into an insert. The assembly of the resonant sensor with the insert is a patch assembly. The sensing region of this sensor desirably extends into the bioreactor for at least 10 millimeters.

In another embodiment depicted in FIG. 6D, the resonant sensor is assembled into an insert. The assembly of the resonant sensor with the insert is a patch assembly. The sensing region of this sensor desirably extends into the bioreactor for at most 2 millimeters. In another embodiment, the resonant sensor is assembled into an insert to form a patch where the patch has the ratio of its diameter to its thickness of at least 10:1 and in one embodiment at least 20:1, and in another embodiment at least 50:1. Some additional non-limiting examples of integration of the sensor into the bioreactor are disclosed in U.S. Pat. No. 8,508,368, "Disposable sensing device having radio frequency based sensor," to Potyrailo et al., which is incorporated by reference in its entirety herein for all purposes.

In any of the disclosed embodiments, the sensor signal is communicated out from the sensor in a suitable manner. For example, in one approach, the sensor signal is communicated via a wired link to the sensor reader and then via a wired link or a wireless link to workstation. In another approach, the sensor signal is communicated via a wired link or a wireless link to the sensor reader and then via a wired link or a wireless link to workstation. "Wireless link" may refer to the communication of an analog or a digital signal via inductive coupling, capacitive coupling, or electromagnetic coupling using radio waves in the radio frequency range from about 30 kHz to 300 GHz.

Figure 7:
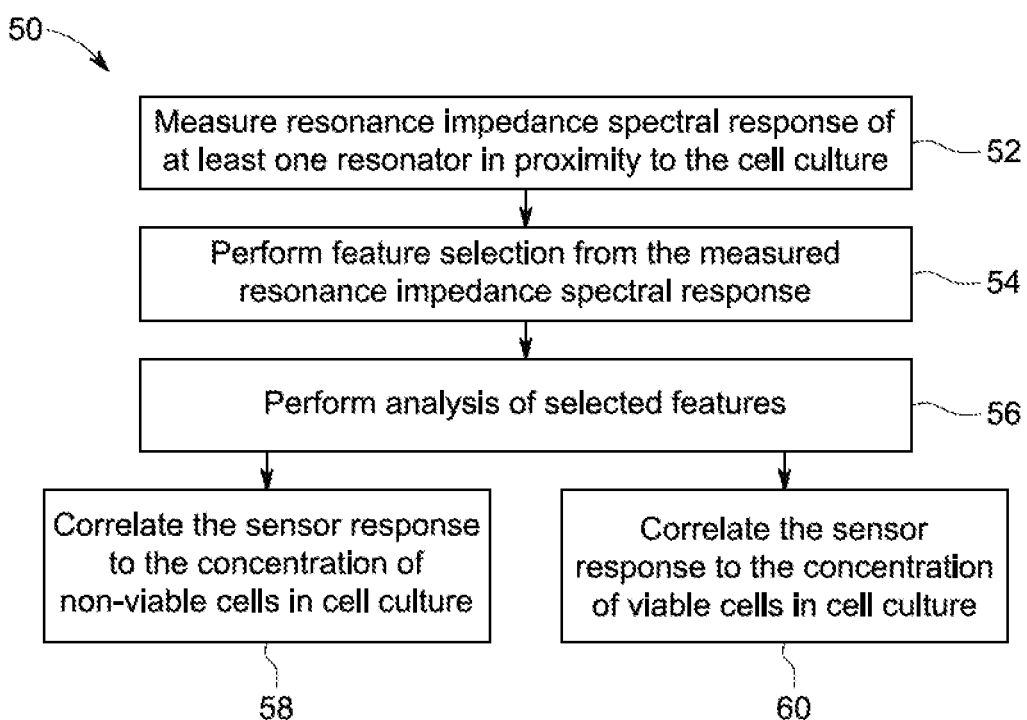
FIG. 7 is a flow diagram of a method of in-line determination of viable and nonviable cells in cell culture according to an embodiment of the disclosure.

FIG. 7 is a flow diagram 50 of a method 50 for simultaneous independent determination and quantitation of viable and nonviable cells in cell culture. At step 52, the sensor 14 measures the resonance impedance spectral response of at least one resonator coupled to the cell culture (e.g., associated with the bioreactor 12). A resonator is a sensor comprising a sensing region and at least one tuning circuit that forms a resonant circuit structure or a resonator. Thus, the resonator coupled to the cell culture is the resonant circuit structure where the sensing region is in operational contact with a cell culture reaction fluid.

At step 54, the method 50 performs feature selection of the measured impedance spectral response and analysis of selected features at step 56. The impedance spectral response can include alpha, beta, gamma, and delta spectral dispersions of cells in a cell culture fluid. Based on the analysis, the sensor response is correlated to the concentration of nonviable cells (step 58) and the concentration of viable cells (step 60). The method 50 may be configured also to provide information about the size of the viable cells. Information about size of viable cells is important for different applications, for example in protein production for vaccines.

The method 50 may be configured to provide outputs to downstream devices or to operators of the system 10. For example, based on the results of the method 50, the system 10 may provide visual indication or readouts to an end user of total numbers of cells, a number or percentage of viable cells, a number or percentage of nonviable cells, a ratio of nonviable cells to viable cells, plots or graphs of viable and nonviable cells over time, or any combination thereof.

In another embodiment, the results of the method 50 may be used to control reaction conditions in the bioreactor 12. For example, if the number of nonviable cells is above a predetermined threshold, the method 50 may also include steps for triggering alarms. In other embodiments, if the total number of cells and the number of viable cells are both above a threshold, the system 10 may be configured to provide instructions for harvesting the cell culture reaction. Further, the results may be used to control reaction conditions (e.g., changing gas and/or feed mixtures, temperature, other conditions) to facilitate a desired ratio of nonviable cells to viable cells.

In particular, the signal acquired from the resonant sensor may include a resonance impedance response spectrum of the sensor from each resonant circuit (e.g., if the sensor 14 includes or operates only a single circuit, the resulting signal includes one spectrum). A plurality of such impedance response spectra may be generated by a plurality of resonant circuits. In one embodiment, viable cells may exhibit a characteristic resonant response that may be distinguished from the resonant response of nonviable cells based on the impedance spectral response that can include alpha, beta, gamma, and delta spectral dispersions of cells in a cell culture fluid. Accordingly, the acquired impedance spectrum or spectra for characteristic patterns may be associated with a particular percentage viability vs. nonviability of cells.

Figure 8:
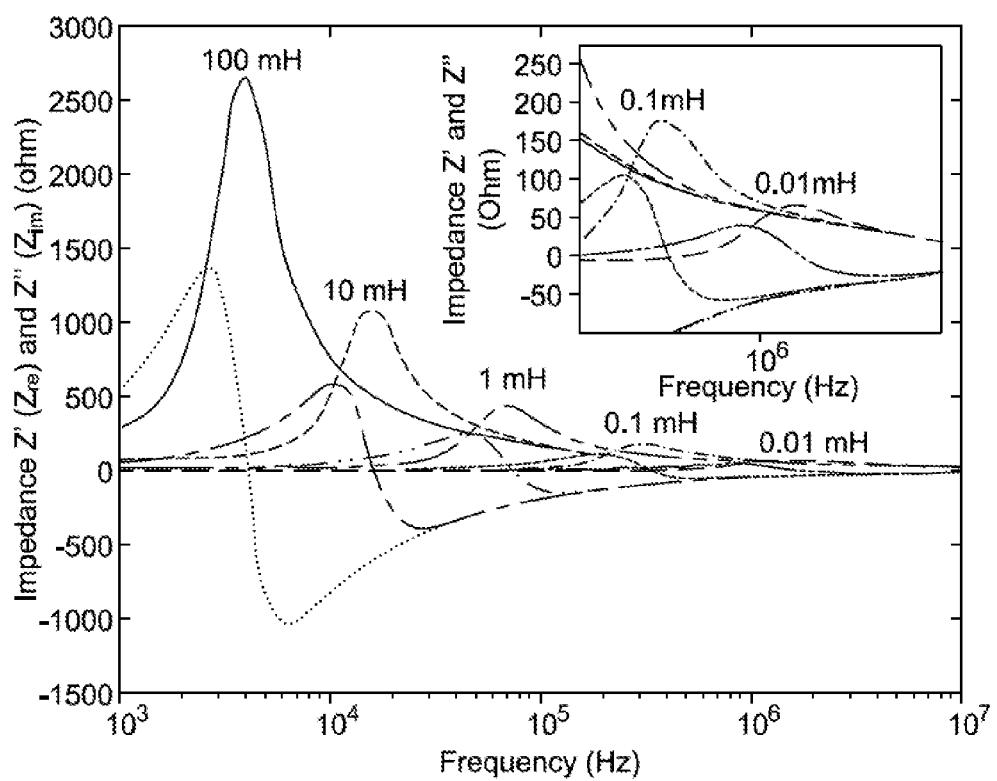
FIG. 8 shows an example of a plot of operation of the sensor at five different resonant frequencies with an inset of a plot of operation of the sensor at two highest resonant frequencies.

FIG. 8 illustrates the operation of a sensor comprising a sensing region and a plurality of tuning circuits that provide five resonances over the frequency range of spectral dispersions of the cell culture. In a non-limiting example, five resonances of the single sensing region are provided by the electronic circuit of the sensor that has five tuned inductor values of 100, 10, 1, 0.1 and 0.01 mH. These inductor values provide the resonances of the single sensing region over the frequency range depicted in FIG. 8.

Figure 9:
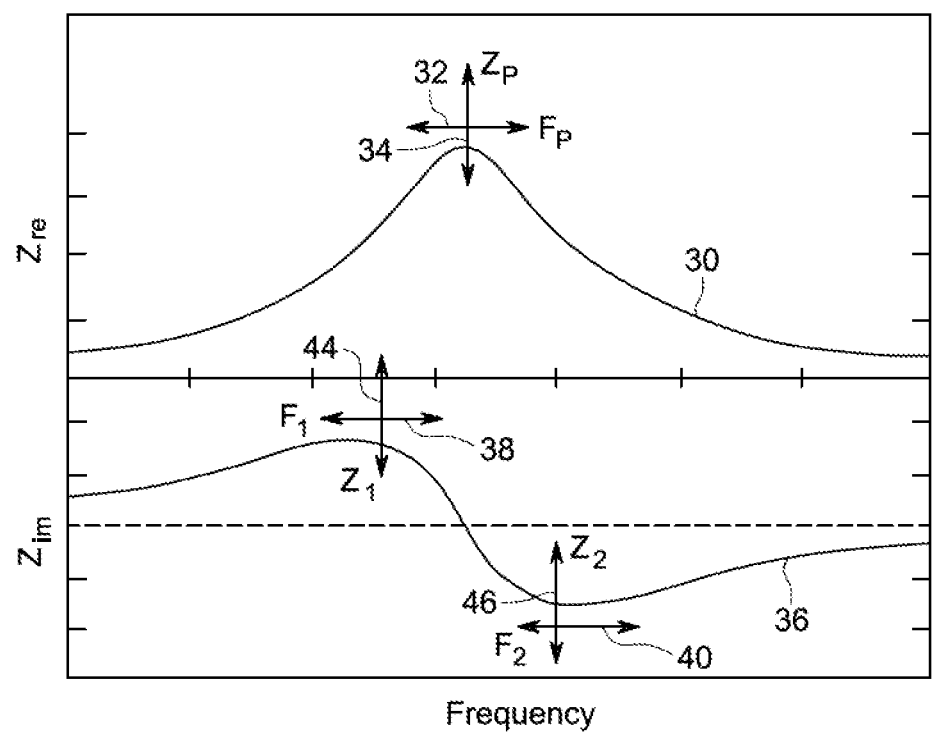
FIG. 9 is a graph of measured impedance parameters of an embodiment of the resonant sensor, in accordance with embodiments of the present technique.

As depicted in FIG. 9, in one embodiment, the system 10 may be configured to measure a resonant impedance 20 $\check{Z}(f)$ (represented by Eq. (1)) of the sensor.

$$\check{Z}(f) = Z_{re}(f) + jZ_{im}(f) \qquad \text{Eq. (1)}$$

where $Z_{re}(f)$ is the real part of the resonant impedance and $Z_{im}(f)$ is the imaginary part of the resonant impedance. In certain embodiments, the impedance response of the sensor may be a multivariable response as more than one frequency may be utilized to measure sensor response across the resonance of the sensor. In certain embodiments, the impedance response of the sensor may be a multivariable response because more than one frequency may be utilized to measure sensor response outside the resonance peak of the sensor. In some embodiments, the sensor response is measured at multiple frequencies across the resonance of the sensor. For example, if the sensor resonates at about 1 MHz, the measured frequencies and associated sensor responses are measured from about 0.25 MHz to about 2 MHz. This multivariable response is analyzed by multivariate analysis. The multivariable response of the sensor includes the sensor's full impedance spectra and/or several individually measured properties, such as but not limited to $F_p, Z_p, F_z, F_1, F_2, Z_1$, and $Z_2$. FIG. 9 depicts a graph of measured impedance parameters of an embodiment of the resonant sensor, in accordance with embodiments of the present technique. These and other measured properties are "spectral parameters". These properties include the frequency of the maximum of the real part of the impedance ($F_p$, resonance peak position), magnitude of the real part of the impedance ($Z_p$, peak height), zero-reactance frequency ($F_z$, frequency at which the imaginary portion of impedance is zero), resonant frequency of the imaginary part of the impedance ($F_1$), and anti-resonant frequency of the imaginary part of the impedance ($F_2$), signal magnitude ($Z_1$) at the resonant frequency of the imaginary part of the impedance ($F_1$), and signal magnitude ($Z_2$) at the anti-resonant frequency of the imaginary part of the impedance ($F_2$). Other parameters may be measured using the entire impedance spectra, for example, quality factor of resonance, phase angle, and magnitude of impedance. Multivariable response spectral parameters are described in U.S. Pat. No. 7,911,345 entitled "Methods and systems for calibration of RFID sensors", which is incorporated herein by reference in its entirety for all purposes.

By using multivariate analysis of full spectra and/or calculated parameters of $\check{Z}(f)$ spectra, quantitation of concentrations of viable and nonviable cells is performed. Also, by using multivariate analysis of full spectra and/or calculated parameters of $\check{Z}(f)$ spectra, determination of size of viable cells and quantitation of concentrations of viable and nonviable cells is performed.

Figure 10A:
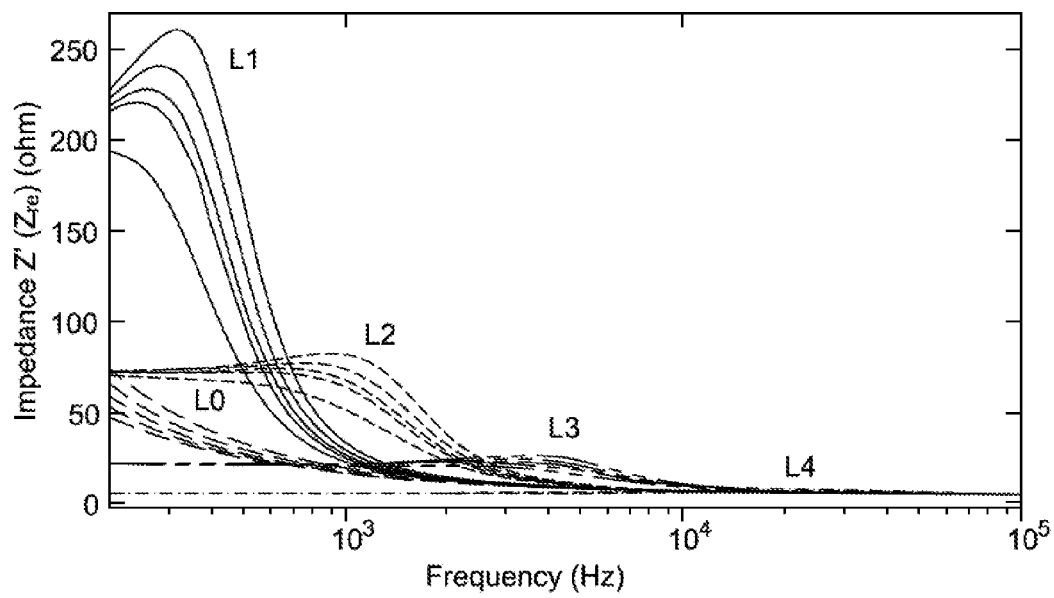
FIG. 10A is a plot of a comparison of conventional and resonance impedance detection with a linear vertical axis.
Figure 10B:
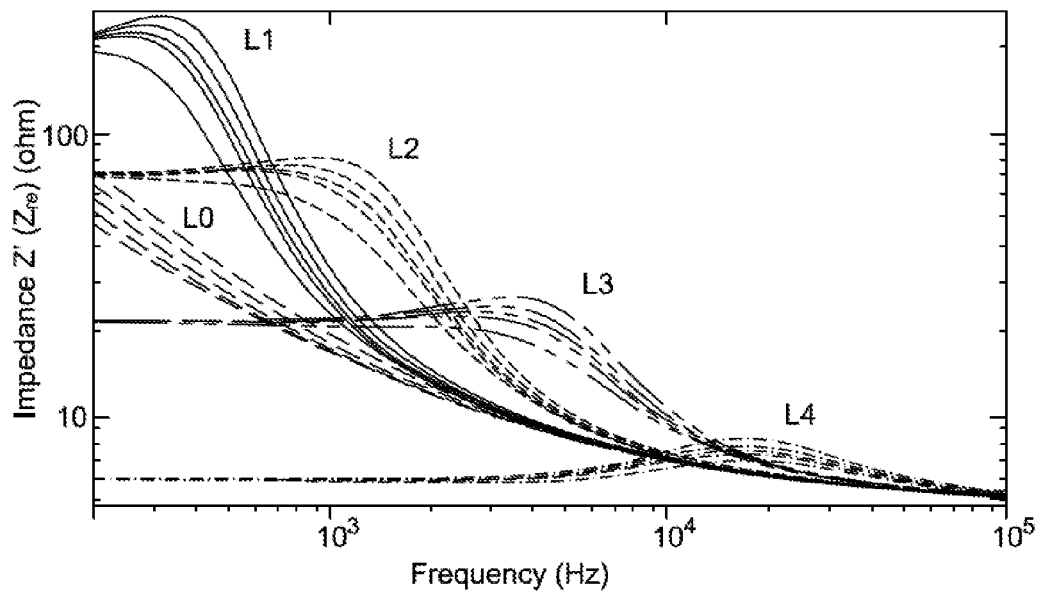
FIG. 10B is a plot of a comparison of conventional and resonance impedance detection with a logarithmic vertical axis.

FIGS. 10A and 10B is a plot of a comparison of conventional and resonance impedance detection during in-line measurements of the varying concentration of cells in the culture. Over the course of these measurements, the conventional and resonance impedance spectra were collected in a rapid sequence. The resonance impedance spectra were generated using four different inductors 1-4 that provided sensor resonances ranging from the smallest frequency to the largest frequency resonances, respectively. Over the time of this experiment, numerous spectra were collected. In FIGS. 10A and B, five time points were chosen to depict the spectral features of the conventional and resonance impedance spectra during the monitoring of the varying concentration of cells in the culture. For clarity, results are illustrated only for the real part Z' (or $Z_{re}$) of impedance. FIG. 10A shows the data with the linear vertical axis, while FIG. 10B shows the data with the logarithmic vertical axis for better depiction of the responses of resonators 3 and 4. Spectra from conventional impedance detection are labeled as L0. Spectra from the resonance impedance detection using inductors 1-4 are labeled as L1, L2, L3, and L4. Individual groups of five spectra of responses L0, L1, L2, L3, and L4 show an increase in their spectral intensity (or impedance) upon an increase of the concentration of cells in the culture.

The resonance impedance detection provides enhanced signal diversity and sensitivity of measurements in cell cultures. First, the signal changes of the resonant responses L1, L2, L3, and L4 (represented as data profiles) are more significant at any particular frequency relative to the conventional impedance data L0 profile. Second, the resonant responses are more diverse in their profiles as illustrates in the changes of the shapes of the resonances L1, L2, L3, and L4.

Figure 11:
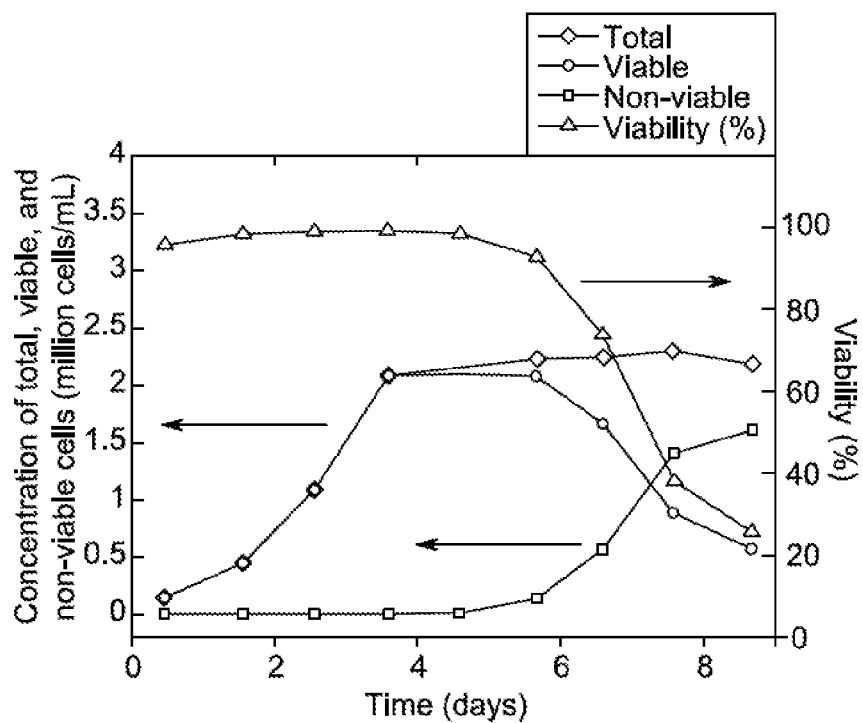
FIG. 11 is a plot of off-line analysis for a cell culture.
Figure 12:
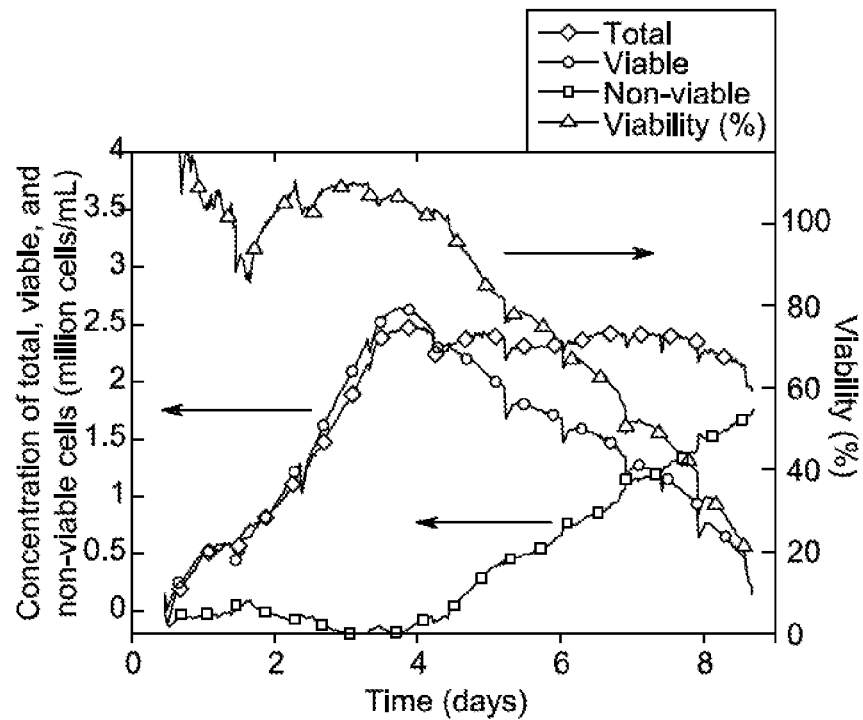
FIG. 12 is a plot of in-line analysis of the cell culture of FIG. 11 according to an embodiment of the disclosure.

FIG. 11 depicts results of the off-line analysis of growth of cells in a typical cell culture run. The cells in this cell culture run were mammalian cells. The off-line analysis was performed using a NucleoCounter NC-100 and it served as a reference data for the evaluation of the developed in-line sensor. Off-line analysis was performed by periodic sampling of the cell culture and performing measurements of the concentration of viable cells, the concentration of nonviable cells, total number of cells (as the sum of viable and nonviable cells), and percent viability of cells (as the ratio of viable to total number of cells multiplied by 100%). A resonant sensor was also positioned directly in this cell culture and in-line measurements were performed with this sensor. FIG. 12 depicts results of the in-line analysis of growth of cells as collected with the resonant sensor. Quantitation of the concentration of viable cells, the concentration of nonviable cells, total number of cells, and percent viability of cells was performed using a well-known partial least squares (PLS) technique of analysis of spectra. The PLS determines correlations between the independent variables and the instrument response by finding the direction in the multidimensional space of the instrument response that explains the maximum variance for the independent variables. A comparison of off-line measurement (FIG. 11) and in-line measurement (FIG. 12) results illustrates a desired correlation between measurements done by off-line and in-line instruments such as measurements of the concentration of viable cells, the concentration of nonviable cells, total number of cells, and percent viability of cells.

In the past, PLS has been used successfully for multivariate analysis of data from an in-line sensor for biomass monitoring of cell culture with scanning dielectric spectroscopy. However, using the earlier reported sensors and univariate and multivariate analysis of data, concentrations of only viable cells were determined quantitatively. Unfortunately, using the earlier reported sensors and univariate and multivariate analysis of data, concentrations of nonviable cells were not determined quantitatively. Only qualitative information was possible to obtain using earlier reported sensors and multivariate analysis of data because the collected spectral data had only at most two multivariable factors. When scanning dielectric spectroscopy data was fitted to a capacitance change of the measured culture, only viable cells were quantitated without ability to quantify nonviable cells. In contrast to those earlier results, the sensors and multivariate analysis of data according to the present techniques provide the quantitative information of not only the viable cells but also the nonviable cells.

In one embodiment, the resonant sensor 14 may be calibrated based on the analysis of off-line parameters or exposure to bioreactors 12 with known percentages of viable cells, upon exposure to a cell culture medium without cells, and upon exposure to a cell culture medium with a known concentration of viable cells. The response of the one or more sensors 14 is measured and an analytical relationship between the environmental parameter and the sensor response is established. The analytical fit coefficients may be calculated using multivariate calibration. In multivariate calibration, more than one property of the sensor response is related to the value of the environmental parameter of interest. Multivariate calibration utilizes the full impedance spectra for calibration, or at least two of individually measured parameters ($Z_p$, $F_p$, $F_z$, $F_1$, $F_2$, $Z_1$, $Z_2$), or at least two of any other parameters that can be extracted from the response of the resonance circuit of the sensor 14. Nonlimiting examples of these additional parameters are quality factor of resonance, phase angle, and magnitude of impedance of the resonance circuit response sensor 14. Nonlimiting examples of multivariate analysis tools are canonical correlation analysis, regression analysis, nonlinear regression analysis, principal components analysis, discriminate function analysis, multidimensional scaling, linear discriminate analysis, logistic regression, pattern matching, and/or neural network analysis. Multivariate calibration can be performed using spectra from conventional impedance measurements, using spectra from resonance impedance measurements, and/or their combinations. Spectra from resonance impedance measurements can include all utilized resonator responses or only a subset of these responses.

The conventional and resonance impedance measurements were compared by measuring sensor responses in model solutions with different solution conductivity and dielectric constant. Such measurements provided the opportunity to quantitatively compare the response of the sensor in its conventional impedance measurement mode and resonant impedance mode. For these measurements, four model solutions were prepared, each having a volume of 200 mL for testing of the sensor response. Solution 1 had 200 mL of water with conductivity of 2 mS/cm. Solution 2 had 200 mL of water with conductivity of 15 mS/cm. Solution 3 had 180 mL of water with conductivity of 2 mS/cm and 20 mL of ethanol. Solution 4 had 180 mL of water with conductivity of 15 mS/cm and 20 mL of ethanol. The dielectric constants of pure water and pure ethanol at room temperature (20° C.) are 80.1 and 24.5, respectively. The dielectric constants of water/ethanol mixtures have respectively changing dielectric constants. Thus, these four model solutions provided the ability to test the response of the sensor to the changes in solution conductivity and dielectric constant. All impedance measurements were done over the range from 1,000 Hz to 10,000,000 Hz. Real and imaginary conventional impedance and resonance impedance spectra of sensor response in four solutions were further processed using a well-known multivariate analysis tool such as principal components analysis (PCA) to determine the similarities and differences between these spectra. Multivariate analysis was performed using a common PLS_Toolbox software (Eigenvector Research, Inc., Wenatchee, Wash.) operated with Matlab software (The Mathworks Inc., Natick, Mass.). The PCA pattern recognition method explains the variance of the data as the weighted sums of the original variables, known as principal components (PCs) or factors. In the past, PCA has been used successfully for multivariate analysis of data from an in-line sensor for biomass monitoring of cell culture with scanning dielectric spectroscopy, where only two PCs were observed from the measured spectra.

FIGS. 13A and B depict the PCA scores plot of PC1 vs. PC2 upon exposure of sensor to four solutions and performing conventional and resonant impedance measurements, respectively. FIG. 13A and FIG. 13B show four clusters of sensor response to four solutions. The clusters are labeled 1, 2, 3, and 4, corresponding to the measured solution. Each cluster has two data points, which are replicates (n=2) of spectral measurements.

FIG. 13A shows that measurements of four solutions using conventional impedance gave good discrimination ability between solutions of low and high conductivity (discrimination between solutions 1 and 2 and solutions 3 and 4). Also, good discrimination ability between different dielectric constants is observed when conductivity of solutions was low (solutions 1 and 3). Unfortunately, discrimination between different dielectric constants when conductivity of solutions was high (solutions 2 and 4) significantly degraded. Data points in clusters 2 and 4 were much closer in the PCA plot as compared to other clusters. In contrast, measurements of four solutions using resonance impedance gave good discrimination ability between all four solutions as depicted in FIG. 13B. The spectral analysis of resonance impedance was performed on all measured resonance peaks. Importantly, the quality of discrimination between solutions with different dielectric constants was similar when solutions were of low dielectric constant (solutions 1 and 3) and high dielectric constant (solutions 2 and 4) as evidenced by the large distances between the respective clusters 1, 2, 3, and 4 (FIG. 13B).

The number of significant factors (principal components) in multivariate data from conventional and resonance impedance measurements was further determined using a common algorithm in PLS_Toolbox software (Eigenvector Research, Inc., Wenatchee, Wash.) operated with Matlab software (The Mathworks Inc., Natick, Mass.). This common algorithm provides an estimate of the number of significant PCA factors for the measured data based on their signal to noise and displays a plot of an estimate of signal to noise for each principal component (factor). The signal to noise of 2 or below of a PC is known to be dominated by noise, while the signal to noise above 3 of a PC is acceptable. The number of factors needed to describe the data is the number of eigenvectors with signal to noise of 3 or greater.

Figure 14A:
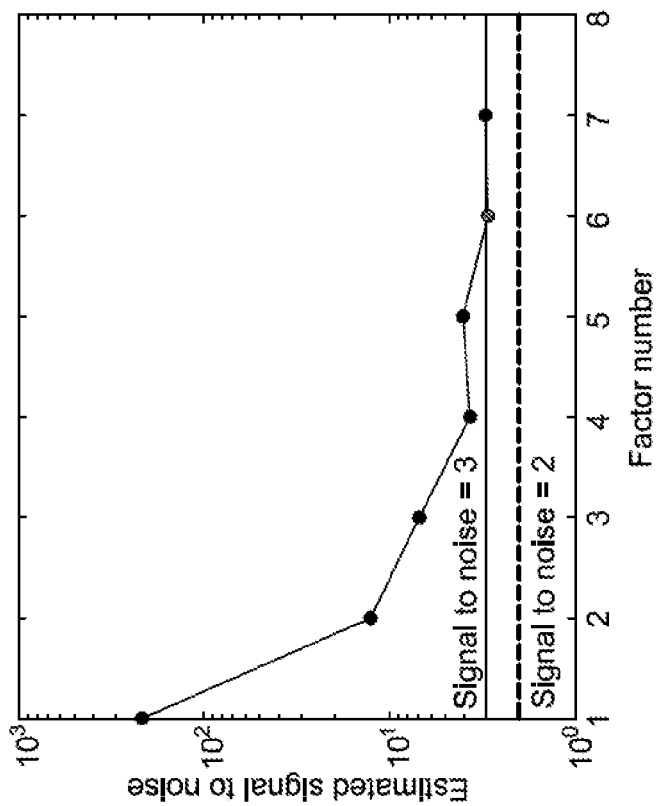
FIG. 14A displays a plot of an estimate of signal to noise for each factor (principal component) for measurements of four solutions using conventional impedance.

FIG. 14A displays a plot of an estimate of signal to noise for each factor (principal component) for measurements of solutions 1-4 using conventional impedance. This plot shows that only the first three factors (principal components) had the signal to noise of three or more, acceptable for a reliable multivariate analysis and quantitations.

Figure 14B:
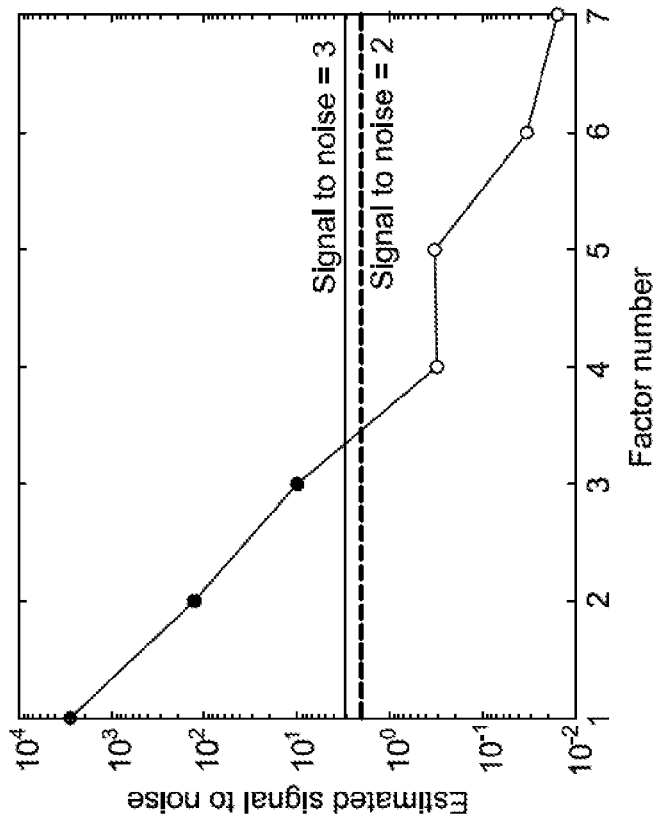
FIG. 14B displays a plot of an estimate of signal to noise for each factor (principal component) for measurements of four solutions using resonant impedance.

FIG. 14B displays a plot of an estimate of signal to noise for each factor (principal component) for measurements of solutions 1-4 using resonant impedance. This plot shows that the first five factors (principal components) had the signal to noise of three or more, acceptable for a reliable multivariate analysis and quantitations. Further, additional factors (principal components) such as PC 6 and PC7 can be also used for multivariate analysis and quantitations because their signal to noise was 3.

Thus, the comparison of signal to noise of different PCs from measurements performed using conventional impedance (FIG. 14A) and resonant impedance (FIG. 14B) showed the higher dimensionality of the multivariable response of the resonant impedance measurements as compared to that of the conventional impedance measurements. The higher dimensionality of the multivariable response of the sensor is related to the higher selectivity of the sensor and sensor ability to more selectively determine larger number of independent environmental conditions affecting the sensor as compared to the sensor with the lower dimensionality of its multivariable response.

In the past, PCA has been used successfully for multivariate analysis of data from an in-line sensor for biomass monitoring of cell culture with scanning dielectric spectroscopy, where only two PCs were observed from the measured spectra. Unlike those earlier results, the sensors may have three (FIG. 14A) and even up to seven (FIG. 14B) PCs useful for the multivariate analysis of frequency spectral data collected using sensors according to the disclosed embodiments.

Detection of viable and nonviable cells can be also described by using an equivalent circuit model of the sensor that includes the cell resistance and capacitance, double layer resistance and capacitance, and solution bulk resistance, as well as the initial sensor resistance, capacitance, and inductance. The exact values of the components of the equivalent circuit are varied in relation to the design of the electrode structure and the existence and type of the protective layer on the sensing region to separate the sensor electrodes from the direct contact with the solution. The equivalent circuit is described by an analytical expression that includes the terms for the real and imaginary portions of at least one resonance impedance spectra of the sensor. The terms in the derived analytical expression are correlated with the total cell concentration and with the viable cell concentration. The terms in the derived analytical expression can be related to the spectral dispersions of the cell culture over the frequency range from 0.1 Hz to 100 GHz and can include alpha, beta, gamma, and delta spectral dispersions.

Figure 15:
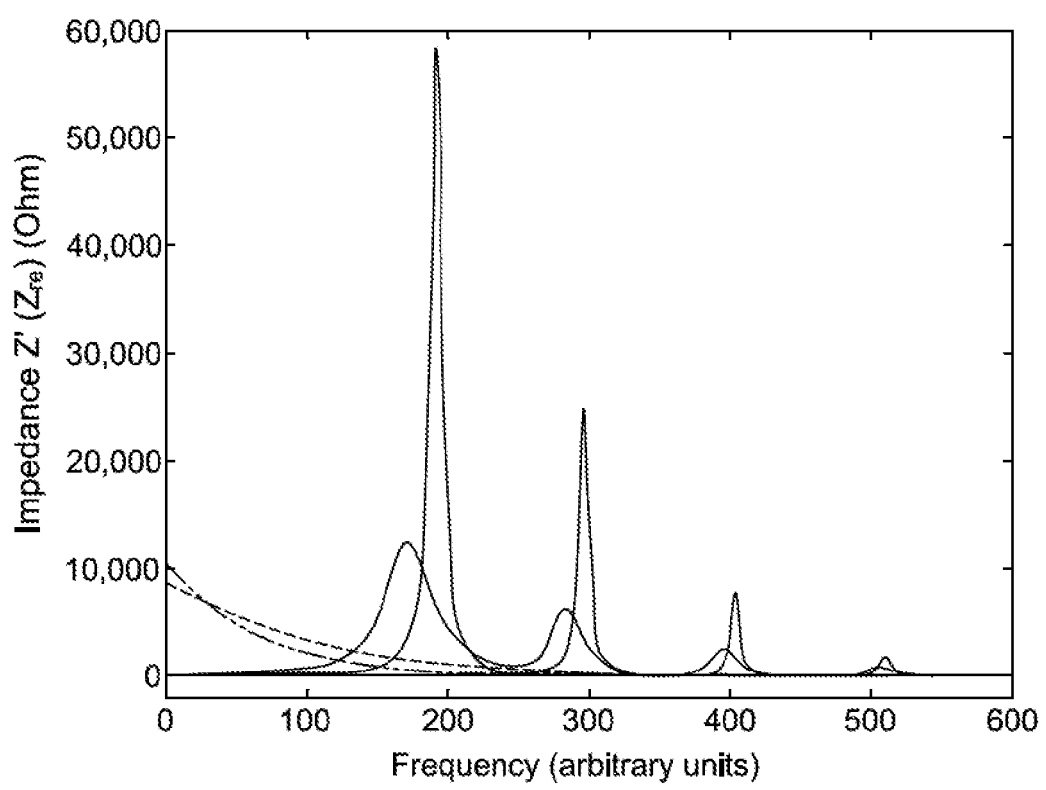
FIG. 15 depicts results of dynamic measurements of a solution over time when the changes in the solution properties were measured using conventional impedance (two dotted lines) and using resonant impedance with four resonators (two solid lines per resonator)
Figure 16A:
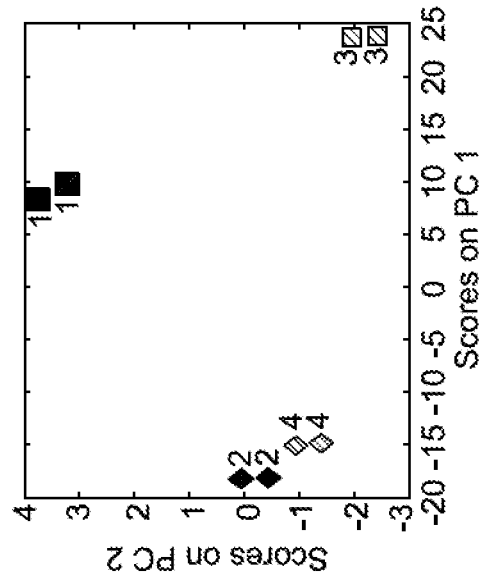
FIG. 16A depicts the PCA scores plot of PC1 vs. PC2 upon measurements of four solutions using a sensor with an inter-digital electrode structure with the electrode width and the spacing between electrodes of 0.45 mm and no dielectric protective coating as measured with conventional impedance.
Figure 16B:
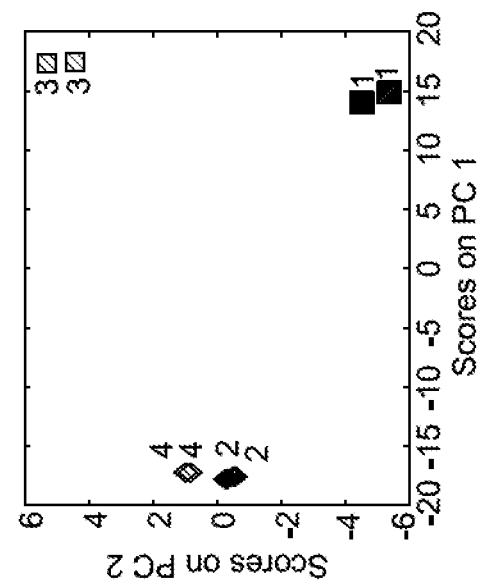
FIG. 16B depicts the PCA scores plot of PC1 vs. PC2 upon measurements of four solutions using a sensor with an inter-digital electrode structure with the electrode width and the spacing between electrodes of 0.45 mm and with a 0.25 micrometers thick dielectric protective coating as measured with conventional impedance.
Figure 16D:
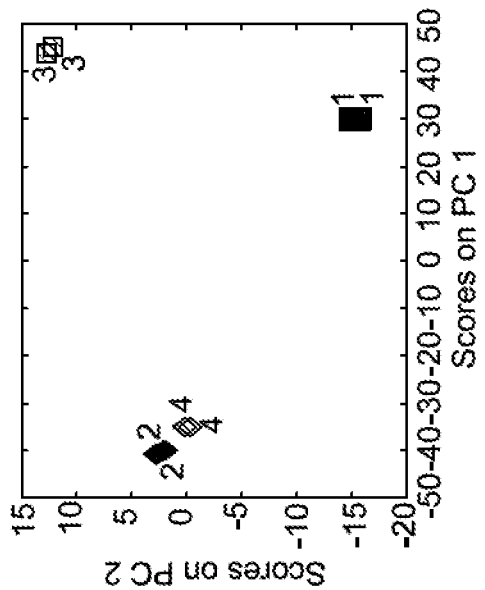
FIG. 16D depicts the PCA scores plot of PC1 vs. PC2 upon measurements of four solutions using a sensor with an inter-digital electrode structure with the electrode width and the spacing between electrodes of 0.45 mm and no dielectric protective coating as measured with resonant impedance.
Figure 16C:
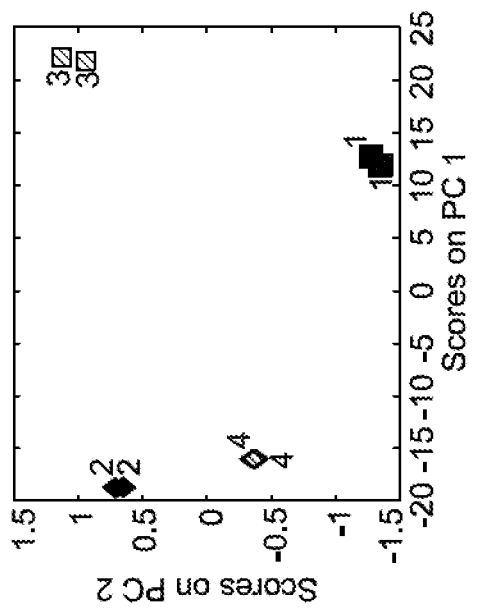
FIG. 16C depicts the PCA scores plot of PC1 vs. PC2 upon measurements of four solutions using a sensor with an inter-digital electrode structure with the electrode width and the spacing between electrodes of 0.45 mm and with a 0.5 micrometers thick dielectric protective coating as measured with conventional impedance.
Figure 16E:
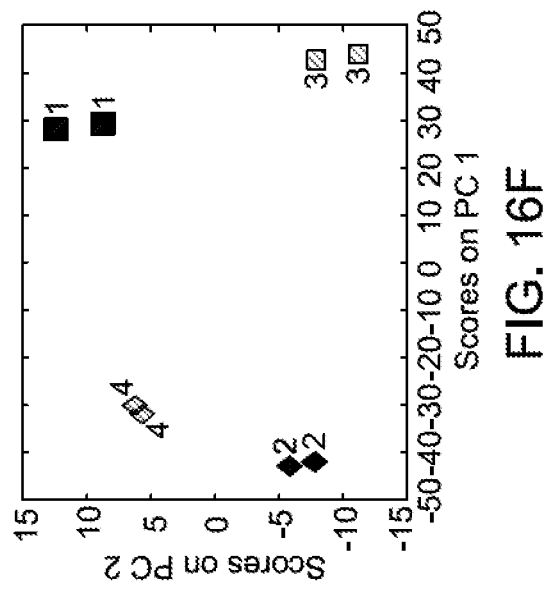
FIG. 16E depicts the PCA scores plot of PC1 vs. PC2 upon measurements of four solutions using a sensor with an inter-digital electrode structure with the electrode width and the spacing between electrodes of 0.45 mm and with a 0.25 micrometers thick dielectric protective coating as measured with resonant impedance.
Figure 16F:
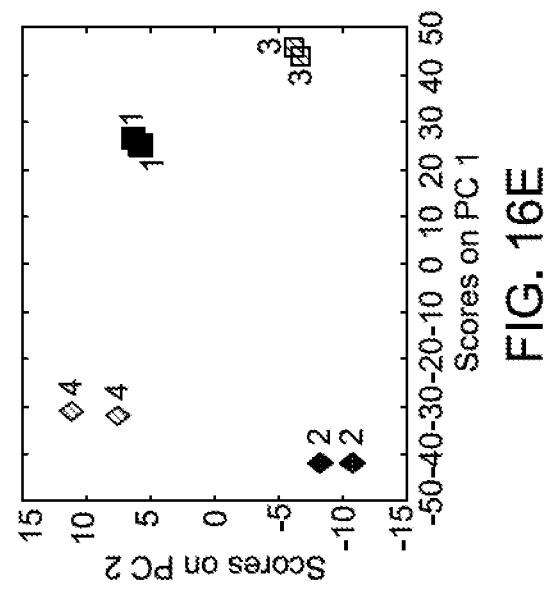
FIG. 16F depicts the PCA scores plot of PC1 vs. PC2 upon measurements of four solutions using a sensor with an inter-digital electrode structure with the electrode width and the spacing between electrodes of 0.45 mm and with a 0.5 micrometers thick dielectric protective coating as measured with resonant impedance.
Figure 17D:
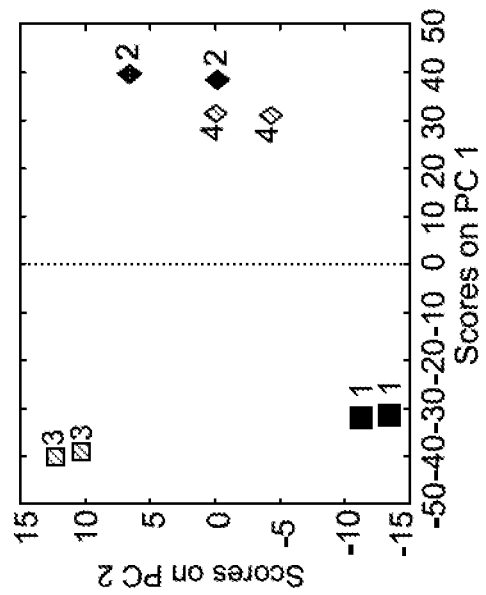
FIG. 17D depicts the PCA scores plot of PC1 vs. PC2 upon measurements of four solutions using a sensor with an inter-digital electrode structure with the electrode width and the spacing between electrodes of 0.3 mm and no dielectric protective coating as measured with resonant impedance.
Figure 17C:
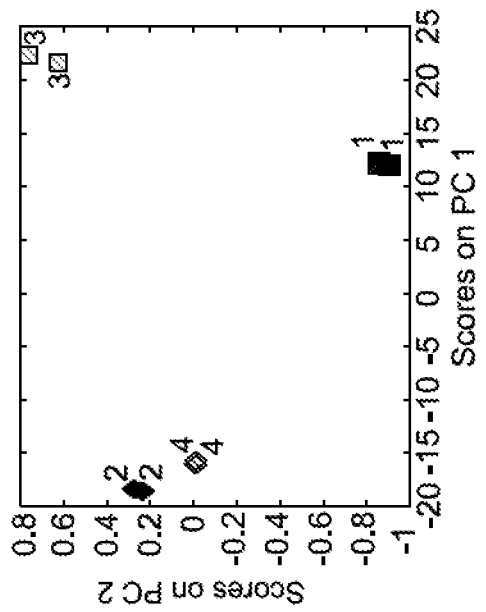
FIG. 17C depicts the PCA scores plot of PC1 vs. PC2 upon measurements of four solutions using a sensor with an inter-digital electrode structure with the electrode width and the spacing between electrodes of 0.3 mm and with a 0.5 micrometers thick dielectric protective coating as measured with conventional impedance.
Figure 17F:
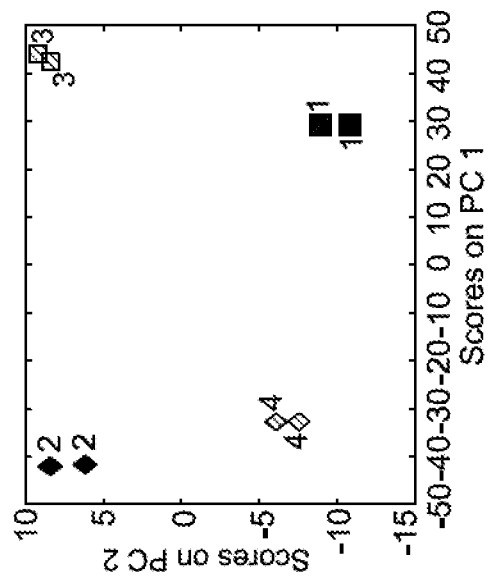
FIG. 17F depicts the PCA scores plot of PC1 vs. PC2 upon measurements of four solutions using a sensor with an inter-digital electrode structure with the electrode width and the spacing between electrodes of 0.3 mm and with a 0.5 micrometers thick dielectric protective coating as measured with resonant impedance.
Figure 17E:
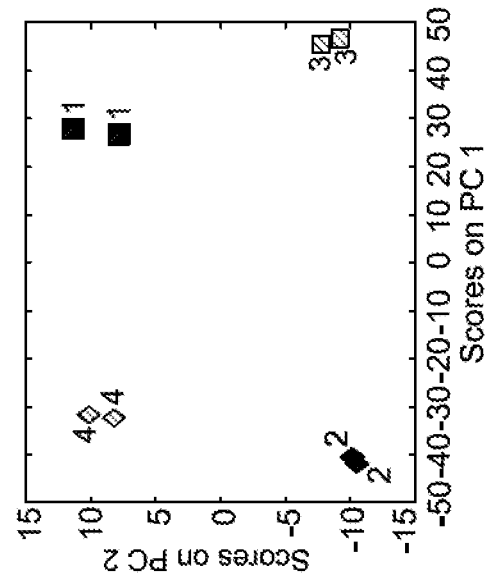
FIG. 17E depicts the PCA scores plot of PC1 vs. PC2 upon measurements of four solutions using a sensor with an inter-digital electrode structure with the electrode width and the spacing between electrodes of 0.3 mm and with a 0.25 micrometers thick dielectric protective coating as measured with resonant impedance.

High detection sensitivity of the resonant impedance measurements has been demonstrated in the present disclosure. When compared to the detection sensitivity of the conventional impedance measurements, sensitivity enhancement of 45-74 fold was achieved depending on the resonator used for sensing. FIG. 15 depicts results of dynamic measurements of a solution over time when the changes in the solution properties were measured using conventional impedance (two dotted lines) and using resonant impedance with four resonators (two dotted lines per resonator). The enhancement of the measurement sensitivity using resonant impedance over conventional impedance was calculated as the impedance response Zre difference between responses measured using a particular resonator divided by the difference between responses measured using conventional impedance at the same frequency range as the resonator. For example, the resonator that operated at the smallest resonant frequency had Zre responses ranging from 58,000 Ohm to 12,500 Ohm over the time of the experiment, while Zre responses measured using conventional impedance were in the range from 1,800 to 800 Ohm over the same experiment time. Thus, the enhancement of sensitivity of the resonant impedance over the conventional impedance measurements was calculated as (58,000−12,500)/(1,800−800)=45. Similarly calculated enhancements of the sensitivity of resonant impedance over conventional impedance measurements for other resonators 2, 3, and 4 were 62, 74, and 46 fold, respectively. Thus, the use of resonant impedance measurements provided a very significant enhancement in sensitivity of measurements over the range of beta-dispersion frequency range of cells. The use of resonant impedance measurements can further provide a significant enhancement in sensitivity of measurements over the range of alpha, beta, gamma, and delta spectral dispersions. The sensor used in this experiment was an interdigital electrode structure coated with a dielectric protective layer. Nonlimiting examples of electrode structures include two- and four-electrode structures. Nonlimiting examples of interdigital electrode structures include two- and four-electrode structures. Nonlimiting examples of materials for electrodes include stainless steel, platinum, gold, noble metals, and others. Nonlimiting examples of materials of a dielectric protective layer include silicon dioxide, silicon nitride, parylene, silicone, fluorinated polymers, ceramics, and others. Nonlimiting examples of fabrication methods of electrodes include metal etching and mask-based metal deposition. Thickness of fabricated electrodes on the substrates is in the range from 10 nanometers to 1000 micrometers.

The importance of the appropriate geometry of the sensing electrode and the associated protective layer has been further evaluated. Two geometries of interdigital electrode structures were fabricated as 1×2 cm structures. These geometries of electrodes are depicted in FIG. 5B and FIG. 5C. In these two types of structures, the electrode width was same as the spacing between electrodes and was 0.45 mm and 0.30 mm. Parylene coating of different thickness was applied onto the electrodes. Coating thickness was 0 micrometers (no coating), 0.25 micrometers, and 0.5 micrometers. For these measurements, four model solutions were prepared, each having a volume of 200 mL for testing of the sensor response. Solution 1 had 200 mL of water with conductivity of 2 mS/cm. Solution 2 had 200 mL of water with conductivity of 15 mS/cm. Solution 3 had 180 mL of water with conductivity of 2 mS/cm and 20 mL of ethanol. Solution 4 had 180 mL of water with conductivity of 15 mS/cm and 20 mL of ethanol. Measurements of conventional impedance and resonance impedance were performed using these sensors. Spectra were analyzed using PCA.

FIG. 16A-F summarize results for the interdigital electrode structures with the electrode width and the spacing between electrodes of 0.45 mm as measured with conventional impedance (FIG. 16 A, B, C) and with resonant impedance (FIG. 16 D, E, F). These interdigital electrode structures had three parylene coating thicknesses of 0, 0.25, and 0.5 micrometers. FIG. 16 A, D depicts results for parylene coating thickness of 0 micrometers (no coating). FIG. 16 B, E depicts results for parylene coating thickness of 0.25 micrometers. FIG. 16 C, F depicts results for parylene coating thickness of 0.5 micrometers.

Similarly, FIG. 17A-F summarize results for the interdigital electrode structures with the electrode width and the spacing between electrodes of 0.3 mm as measured with conventional impedance (FIG. 17 A, B, C) and with resonant impedance (FIG. 17 D, E, F). These interdigital electrode structures had three parylene coating thicknesses of 0, 0.25, and 0.5 micrometers. FIG. 17 A, D depicts results for parylene coating thickness of 0 micrometers (no coating). FIG. 17 B, E depicts results for parylene coating thickness of 0.25 micrometers. FIG. 17 C, F depicts results for parylene coating thickness of 0.5 micrometers.

FIGS. 16A-F and 17A-F illustrate that applying a protective coating improves the separation between the spectral response clusters related to the different dielectric constants and conductivities of measured solutions.

Technical effects of the disclosed embodiments include an in-line and real-time technique for assessing cell viability in a cell culture. Such techniques facilitate distinguishing between viable and nonviable cells, which provides a benefit over biomass-type sensors, which do not distinguish between viable and nonviable cells.

This written description uses examples, including the best mode, and also to enable any person skilled in the art to practice the embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for assessing a cell culture reaction fluid of a cell culture reaction, comprising the steps of:
generating a plurality of frequencies with a sensor comprising a sensing region in operational contact with the cell culture reaction fluid and a plurality of tuning circuits outside the fluid;
receiving a signal from the sensor, wherein the signal is representative of impedance spectra of the sensing region in operational contact with the cell culture reaction fluid over a measured spectral frequency range;
analyzing the impedance spectra; and
determining one or more properties of the cell culture reaction fluid based on the analyzed impedance spectra.

2. The method of claim 1, wherein the impedance spectra comprise resonance impedance spectra.

3. The method of claim 1, wherein the tuning circuits comprise inductors.

4. The method of claim 1, wherein the plurality of frequencies generate an impedance response over a frequency range of spectral beta dispersion of the cell culture reaction.

5. The method of claim 1, wherein the plurality of frequencies generate an impedance response over a frequency range of spectral alpha, beta, gamma, and/or delta dispersion of the cell culture reaction.

6. The method of claim 1, wherein the plurality of frequencies generate a resonant response over a frequency range of spectral beta dispersion of the cell culture reaction.

7. The method of claim 1, wherein the plurality of frequencies comprise at least three frequencies over a frequency range of spectral beta dispersion of the cell culture reaction.

8. The method of claim 1, wherein the sensing region is in direct contact with the cell culture reaction fluid.

9. The method of claim 1, wherein the sensing region is separated from the cell culture reaction by a dielectric protective layer.

10. The method of claim 9, wherein the dielectric protective layer has thickness from 10 nanometers to 10 millimeters.

11. The method of claim 1, wherein analyzing the impedance spectra comprises analyzing at least six spectral parameters of each of impedance spectrum.

12. The method of claim 1, wherein analyzing the impedance spectra comprises analyzing at least six spectral parameters of each of impedance spectrum that include resonance parameters Fp, Zp, F1, Z1, F2, Z2.

13. The method of claim 1, wherein analyzing the impedance spectra comprises analyzing of at least real part of the impedance and/or imaginary part of the impedance.

14. The method of claim 1, wherein the step of analyzing the impedance spectra further comprises the step of determining a linear combination of spectral parameters of the measured impedance spectra.

15. The method of claim 1, wherein the step of analyzing the impedance spectra further comprises the step of fitting the impedance spectra to the equivalent circuit model.

16. The method of claim 1, wherein the step of determining the properties of the cell culture reaction further comprises the step of determining a concentration of viable cells and a concentration of nonviable cells in the cell culture reaction.

17. The method of claim 1, wherein the step of determining the properties of the cell culture reaction further comprises the step of determining a concentration of viable cells, a concentration of nonviable cells, and diameter of viable cells in the cell culture reaction.

18. The method of claim 1, wherein the step of determining the properties of the cell culture reaction further comprises the step of determining cell culture productivity in measurement of a concentration of viable and a concentration of nonviable cells.

* * * * *